(12) United States Patent
Dai et al.

(10) Patent No.: US 11,785,841 B2
(45) Date of Patent: Oct. 10, 2023

(54) COMPOUND, DISPLAY PANEL AND DISPLAY APPARATUS

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Wenpeng Dai, Shanghai (CN); Wei Gao, Shanghai (CN); Jinghua Niu, Shanghai (CN); Lei Zhang, Shanghai (CN); Yang Li, Shanghai (CN); Dongyang Deng, Shanghai (CN); Ping An, Shanghai (CN)

(73) Assignees: WUHAN TIANMA MICROELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 792 days.

(21) Appl. No.: 16/732,136

(22) Filed: Dec. 31, 2019

(65) Prior Publication Data

US 2020/0373493 A1    Nov. 26, 2020

(30) Foreign Application Priority Data

May 24, 2019  (CN) .......................... 201910441335.X

(51) Int. Cl.
*H10K 85/60*       (2023.01)
*C07D 401/10*      (2006.01)
(Continued)

(52) U.S. Cl.
CPC ......... *H10K 85/615* (2023.02); *C07D 401/10* (2013.01); *C07D 403/08* (2013.01);
(Continued)

(58) Field of Classification Search
CPC ............. H01L 51/0052; H01L 51/0054; H01L 51/0067; H01L 51/0072; H01L 51/5012; H01L 51/5016; H01L 51/5056; H01L 51/5072; H01L 2251/552; H01L 51/0085; H01L 51/0059; H01L 51/007; H01L 51/0071; H01L 51/0073; H01L 51/0074; H01L 51/0094; C07D 401/10; C07D 403/08; C07D 403/14; C07D 209/86; C07D 213/36; C07D 219/02; C07D 239/26; C07D 251/24; C07D 265/38; C07D 279/22; C07D 401/14; C07D 403/10; C07D 405/14; C07D 409/08; C07D 409/14; C07D 413/14; C07D 417/14; C07D 487/04; C07D 491/048; C07D 493/04; C07D 495/04; C09K 11/06; C09K 2211/1018; C07C 255/58; C07C 2603/74; C07F 5/027; C07F 7/10; C07F 9/5728; C07F 9/65586; H10K 85/615;
(Continued)

(56) References Cited

U.S. PATENT DOCUMENTS 6,777,111 B1 *   8/2004   Tanaka ................ H01L 51/0058
                                              313/506

FOREIGN PATENT DOCUMENTS

CN       102482571 A  *  5/2012  ........... C07D 401/04
CN       102482571 A      5/2012
(Continued)

OTHER PUBLICATIONS

CAS reg. No. 2410617-23-9, Feb. 27, 2020. (Year: 2020).*
(Continued)

*Primary Examiner* — Douglas J McGinty
(74) *Attorney, Agent, or Firm* — CHRISTENSEN O'CONNOR JOHNSON KINDNESS PLLC

(57) ABSTRACT

A compound having a D-($\pi$)-$\sigma$-($\pi$)-A chemical structure and improving brightness and efficiency of light-emitting is described. In an embodiment, the compound has a chemical structure according to Formula (I), in which $L_1$ and $L_2$ are each at least one of a single bond, C1-C20 alkylene, C3-C20 cycloalkylene, C3-C20 heterocyclic alkylene, C6-C40 arylene, C4-C40 heteroarylene, C10-C60 fused arylene, or C10-C60 fused heteroarylene; the electron donor D is C1-C20 alkyl, C3-C20 cycloalkyl, C1-C20 alkoxy, C3-C20 heterocyclic group, C6-C40 aryl, C4-C40 heteroaryl, C10-C60 fused arylene, C10-C60 fused heteroarylene, C12-C40 carbazolyl and its derivative groups, C12-C40 diphenylamino and its derivative groups, C18-C60 triphenylamino and its derivative groups, or C12-C40 acridinyl and its derivative groups; and the electron acceptor A is a nitrogen-containing heterocyclic group, a cyano-containing group, a triarylboron-based group, a benzophenone-based group, an aromatic heterocyclic ketone-based group, a sulfone-based group, or a phosphoroso-containing groups.

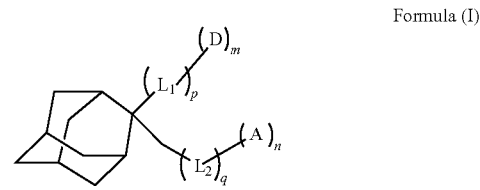

Formula (I)

13 Claims, 2 Drawing Sheets

(51) Int. Cl.
  *C07D 403/08* (2006.01)
  *C07D 403/14* (2006.01)
  *C09K 11/06* (2006.01)
  *H10K 50/11* (2023.01)
  *H10K 50/15* (2023.01)
  *H10K 50/16* (2023.01)
  *H10K 101/10* (2023.01)
  *H10K 101/30* (2023.01)

(52) U.S. Cl.
  CPC ............ *C07D 403/14* (2013.01); *C09K 11/06* (2013.01); *H10K 85/622* (2023.02); *H10K 85/654* (2023.02); *H10K 85/6572* (2023.02); *C09K 2211/1018* (2013.01); *H10K 50/11* (2023.02); *H10K 50/15* (2023.02); *H10K 50/16* (2023.02); *H10K 2101/10* (2023.02); *H10K 2101/30* (2023.02)

(58) Field of Classification Search
  CPC ............ H10K 85/622; H10K 85/654; H10K 85/6572; H10K 50/11; H10K 50/15; H10K 50/16; H10K 2101/10; H10K 2101/30; H10K 85/342; H10K 85/631; H10K 85/40; H10K 85/6565; H10K 85/657; H10K 85/6574; H10K 85/6576
  USPC ........................................................ 428/690
  See application file for complete search history.

(56) References Cited

FOREIGN PATENT DOCUMENTS

EP     1202608 A2    5/2002
WO    2017/205425 A1  11/2017

OTHER PUBLICATIONS

First Chinese Office Action dated Aug. 1, 2022, issued in corresponding Chinese Application No. 201910441335.X, filed on May 24, 2019, 24 pages.

Fukagawa, H., et al., "Novel Hole-Transporting Materials with High Triplet Energy for Highly Efficient and Stable Organic Light-Emitting Diodes," The Journal of Physical Chemistry, 2016, 120, 18748-18755.

\* cited by examiner

COMPOUND, DISPLAY PANEL AND DISPLAY APPARATUS

CROSS-REFERENCE TO RELATED APPLICATIONS

The present application claims priority to Chinese Patent Application No. 201910441335.X, filed on May 24, 2019, the content of which is incorporated herein by reference in its entirety.

TECHNICAL FIELD

The present disclosure relates to the field of organic electroluminescent materials, and particularly, to a compound, a display panel and a display apparatus including the compound.

BACKGROUND

As a new generation of display technology, organic electroluminescent materials such as organic light-emitting diodes (OLED) have been widely applied in flat-panel displays, flexible displays, solid-state lighting and vehicle displays, due to their advantages of smaller thickness, self-illumination, wide viewing angle, fast response, high efficiency, good temperature adaptability, simple manufacturing process, low drive voltage, low energy consumption and the like.

Electroluminescence can be classified into electrofluorescence and electrophosphorescence depending upon the luminescence mechanism. Fluorescence is a result of a radiation attenuation transition of singlet excitons, and phosphorescence is a result of light emitted during attenuation transition to the ground state of triplet excitons. According to the spin-statistics theoretical, a probability ratio of forming singlet excitons and triplet excitons is 1:3. The internal quantum efficiency of the electrofluorescent material is no more than 25%, and the external quantum efficiency is generally less than 5%. Theoretically, the internal quantum efficiency of the electrophosphorescent material can reach 100%, and the external quantum efficiency can be up to 20%. In 1998, Professor Yuguang Ma from Jilin University in China and Professor Forrest from Princeton University in the United States both reported that ruthenium complexes and platinum complexes were used as dyes doped into the light-emitting layer, a phenomenon of electrophosphorescence was explained, and applied the prepared phosphorescent material to an electroluminescent device.

The long lifetime (μs) of phosphorescent heavy metal materials may lead to triplet state-triplet state quenching and concentration quenching at high current densities and further result in a degradation of device performance. Therefore, phosphorescent heavy metal materials are usually doped into suitable host materials to form a host-guest doping system. In this way, energy transfer is enhanced, and light-emitting efficiency and lifetime are increased. At present, heavy metal doping materials have been commercialized, and however, development of alternative doping materials has proven challenging. Thus, it is urgent to develop a novel phosphorescent host material.

SUMMARY

In view of this, the present disclosure provides a bipolar compound having a structure of D-(π)-σ-(π)-A. The compound has a chemical structure according to Formula (I):

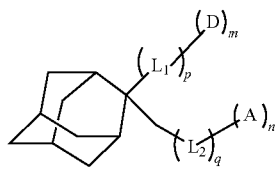

wherein D is an electron donor, A is an electron acceptor; m is a number of the electron donors D, n is a number of the electron acceptors A, and m and n are each an integer respectively selected from 1, 2 or 3; p is a number of $L_1$, q is a number of $L_2$, and p and q are each an integer respectively selected from 0, 1, or 2;

$L_1$ and $L_2$ are each independently selected from the group consisting of a single bond, a substituted or unsubstituted C1-C20 alkylene, a substituted or unsubstituted C3-C20 cycloalkylene, a substituted or unsubstituted C3-C20 heterocyclic alkylene, a substituted or unsubstituted C6-C40 arylene, a substituted or unsubstituted C4-C40 heteroarylene, a substituted or unsubstituted C10-C60 fused arylene, a substituted or unsubstituted C10-C60 fused heteroarylene, and combinations thereof;

D is selected from the group consisting of a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C4-C40 heteroaryl, a substituted or unsubstituted C10-C60 fused arylene, a substituted or unsubstituted C10-C60 fused heteroarylene, a substituted or unsubstituted C12-C40 carbazolyl and its derivative groups, a substituted or unsubstituted C12-C40 diphenylamino and its derivative groups, a substituted or unsubstituted C18-C60 triphenylamino and its derivative groups, a substituted or unsubstituted C12-C40 acridinyl and its derivative groups, and combinations thereof; and A is selected from the group consisting of a nitrogen-containing heterocyclic group, a cyano-containing group, a triarylboron-based group, a benzophenone-based group, an aromatic heterocyclic ketone-based group, a sulfone-based group, a phosphoroso-containing groups, and combinations thereof.

The present disclosure also provides a display panel, including an organic light-emitting device. The organic light-emitting device includes an anode, a cathode arranged opposite to the anode, a capping layer disposed at a side of the cathode facing away from the anode, and an organic layer disposed between the anode and the cathode, the organic layer comprising an electron transmission layer, a hole transmission layer, and a light-emitting layer, wherein at least one of the capping layer, the electron transmission layer, the hole transmission layer, and the light-emitting layer is made of the compound according to the present disclosure.

The present disclosure further provides a display apparatus including the display panel according to the present disclosure.

DESCRIPTION OF EMBODIMENTS

Figure 1:
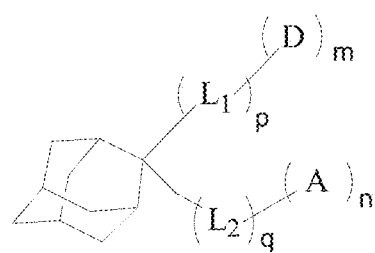
FIG. 1 is a chemical formula of a compound according to an embodiment of the present disclosure.
Figure 2:
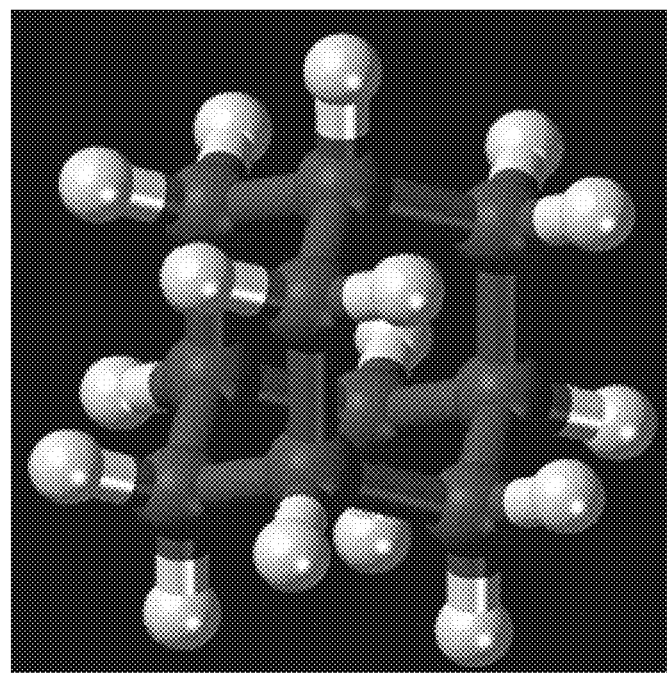
FIG. 2 is a structural schematic diagram of a compound according to an embodiment of the present disclosure, in which adamantane acts as a mother nucleus structure.

The present disclosure is further described in combination with the following examples and comparative examples, which are merely intended to explain the present disclosure. The present disclosure is not limited to the following examples.

An of the present disclosure provides a compound having a chemical structure according to Formula (I):

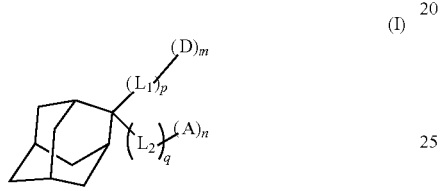

(I)

wherein D is an electron donor, A represents an electron acceptor; m is a number of D, n is a number of A, and m and n are each an integer respectively selected from 1, 2 or 3; p is a number of $L_1$, q is a number of $L_2$, and p and q are each an integer independently selected from 0, 1, or 2;

$L_1$ and $L_2$ are each independently selected from the group consisting of a single bond, a substituted or unsubstituted C1-C20 alkylene, a substituted or unsubstituted C3-C20 cycloalkylene, a substituted or unsubstituted C3-C20 heterocyclic alkylene, a substituted or unsubstituted C6-C40 arylene, a substituted or unsubstituted C4-C40 heteroarylene, a substituted or unsubstituted C10-C60 fused arylene, a substituted or unsubstituted C10-C60 fused heteroarylene, and combinations thereof;

D is selected from the group consisting of a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C4-C40 heteroaryl, a substituted or unsubstituted C10-C60 fused arylene, a substituted or unsubstituted C10-C60 fused heteroarylene, a substituted or unsubstituted C12-C40 carbazolyl and its derivative groups, a substituted or unsubstituted C12-C40 diphenylamino and its derivative groups, a substituted or unsubstituted C18-C60 triphenylamino and its derivative groups, a substituted or unsubstituted C12-C40 acridinyl and its derivative groups, and combinations thereof; and A is selected from the group consisting of a nitrogen-containing heterocyclic group, a cyano-containing group, a triarylboron-based group, a benzophenone-based group, an aromatic heterocyclic ketone-based group, a sulfone-based group, a phosphoroso-containing groups, and combinations thereof.

The compound provided by the present disclosure is a bipolar material having a D-(π)-σ-(π)-A structure, which can replace the traditional D-π-A bipolar material and has strong intramolecular charge transmission, resulting in a large dipole moment μs. The organic compound having the D-(π)-σ-(π)-A structure also have bipolar properties, and the central σ bond can effectively interrupt the transmission between the donor D and the acceptor A, so that an excited state is limited as a local excited state within a segment of donor D or acceptor A. Therefore, the compound has a smaller excited state dipole moment, and can improve luminance and light-emitting efficiency EQE.

The compound of the present disclosure, as a phosphorescent host material, can satisfy the following design characteristics:

(i) the host material has a higher triplet energy level $E_T$ than the guest material, preventing a backflow of triplet energy from the guest material to the host material, thereby limiting triplet excitons within a light-emitting layer to the maximal extent;

(ii) HOMO and LUMO levels of the host material match energy levels of the materials of the adjacent layer, such that hole and electron injections barriers and a driving voltage of the device can be reduced. In addition, an energy level difference Eg between HOMO level and LUMO level of the host material should be greater than an energy level difference Eg between HOMO level and LUMO level of the guest material, which is beneficial to an energy transfer from the host material to the guest material and a direct capture of carriers on the phosphorescent guest material;

(iii) the host material has a high carrier transmission rate and a balanced-carrier-transmission properties, which facilitates the balance of hole and electron transmission in the device while obtaining a wide carrier recombination region, thereby improving the light-emitting efficiency; and (iv) the host material has a good thermal stability, film formability, and an appropriate glass transition temperature Tg that facilitate a formation of a stable and uniform film during thermal vacuum vapor-deposition while reducing phase separation and maintaining device stability.

When the compound provided by the present disclosure is used as a host material in an electroluminescence device, it can improve balanced migration of carriers, widen an exciton recombination region, and improve light extraction efficiency due to its high triplet energy level $E_T$, relatively high molecular density, high glass transition temperature, and high molecular thermal stability. Therefore, light-emitting efficiency and service time of the device can be significantly improved, and thus can be applied in the electroluminescent device.

Adamantane in the compound of the present disclosure has a chemical name of tri-cyclo [3,3,1,13,7]decane, which is a tetrahedral cyclic hydrocarbon composed of 10 carbon atoms and 16 hydrogen atoms. It is a colorless crystal, and has a melting point of 268° C., a relative density of 1.07, and a refractive index of 1.568. It is non-toxic, odorless, easy to sublimate, insoluble in water, and slightly soluble in benzene. A unit composition of adamantane is a chair-like conformation of cyclohexane, and the entire ring has characteristics of symmetry and rigidity. Adamantane is an alicyclic carbohydrate having 10 carbon atoms and having the same structure as adamas. Since its structural unit is chair-like cyclohexane, it has an orderly structure, an excellent transparency and stability. Generally, adamantane does not react with nitric acid and potassium permanganate, but the hydrogen atoms in the molecule are sensitive to a SN1 type nucleophilic substitution reaction and SE2 type electrophilic substitution reaction. In addition, under certain conditions, molecules of adamantane may undergo reactions such as backbone rearrangement, oxidation, alkylation, or the like. Therefore, they are widely applied in medicine, functional polymers, lubricants, surfactants, catalysts, photographic materials, and the like, being known as a new generation of fine chemical raw materials.

According to an embodiment of the present disclosure, $L_1$ and $L_2$ are identical.

According to an embodiment of the present disclosure, $L_1$ and $L_2$ are different.

According to an embodiment of the present disclosure, p is 0, and q is 1.

According to an embodiment of the present disclosure, m and n are each 1.

According to an embodiment of the present disclosure, D is any one of the following formulas:

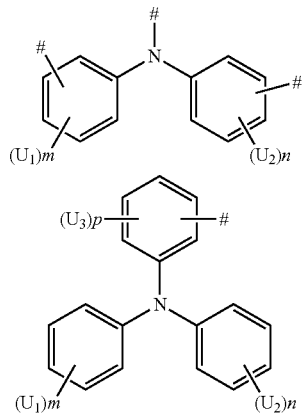

wherein m, n and p are each an integer independently selected from 0, 1, 2 or 3;

$U_1$, $U_2$, and $U_3$ are each independently selected from the group consisting of a hydrogen atom, a substituted or unsubstituted C1-C30 alkyl, a substituted or unsubstituted silylene, a substituted or unsubstituted C3-C20 cycloalkyl, a substituted or unsubstituted C1-C30 alkoxy, a substituted or unsubstituted C6-C30 aryl, a substituted or unsubstituted C10-C30 fused aryl, and combinations thereof; and # indicates a bonding position.

According to an embodiment of the present disclosure, D is any one of the following groups:

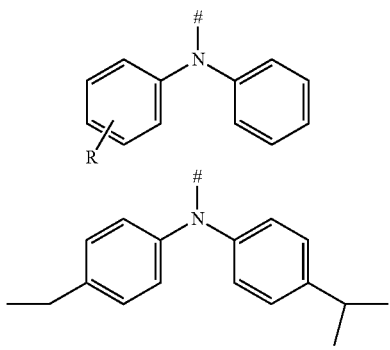

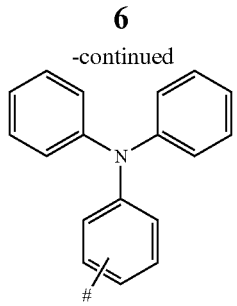

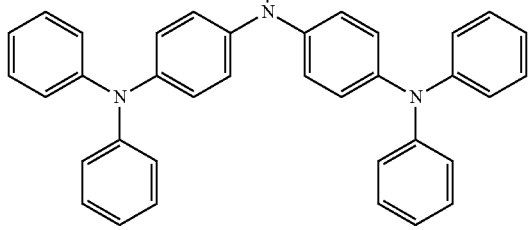

wherein R is selected from the group consisting of a hydrogen atom, a substituted or unsubstituted C1-C20 alkyl, a substituted or unsubstituted silylene, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C10-C30 fused aryl, and a substituted or unsubstituted C4-C40 heteroaryl.

According to an embodiment of the present disclosure, D is any one of the following groups:

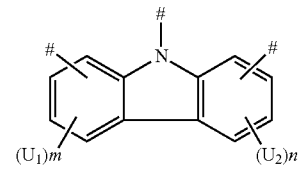

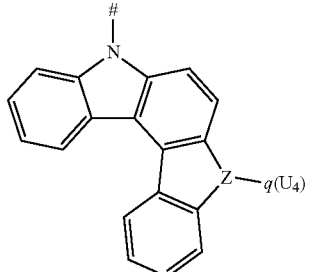

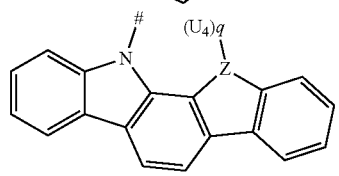

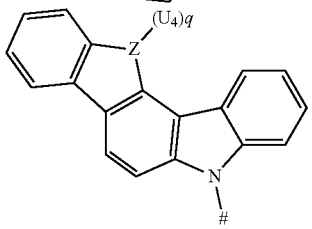

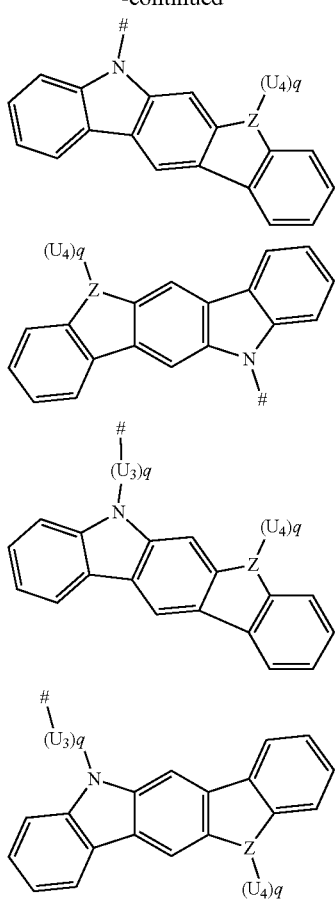

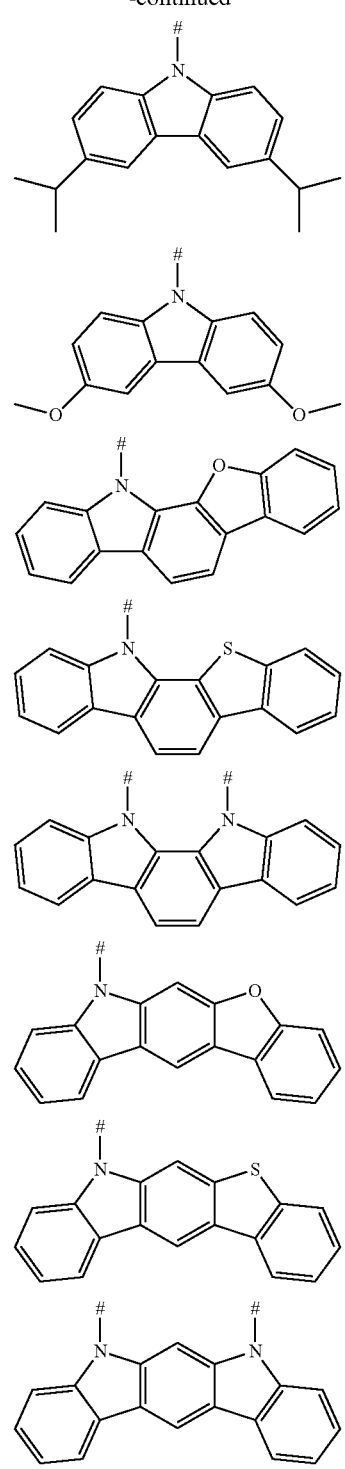

wherein Z is selected from the group consisting of a carbon atom, a nitrogen atom, an oxygen atom, a sulfur atom and a silicon atom;

m, n and q are each an integer independently selected from 0, 1, 2 or 3;

$U_1$, $U_2$, $U_3$ and $U_4$ are each independently selected from the group consisting of a hydrogen atom, a substituted or unsubstituted C1-C30 alkyl, a substituted or unsubstituted silylene, a substituted or unsubstituted C3-C20 cycloalkyl, a substituted or unsubstituted C1-C30 alkoxy, a substituted or unsubstituted C6-C30 aryl, a substituted or unsubstituted C10-C30 fused aryl, and combinations thereof;

when Z is an oxygen atom or a sulfur atom, q is 0; and # indicates a bonding position.

According to an embodiment of the present disclosure, D is any one of the following groups:

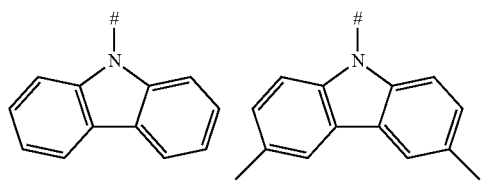

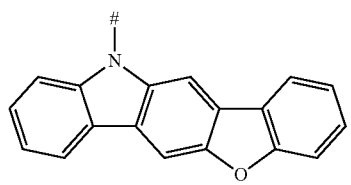

-continued

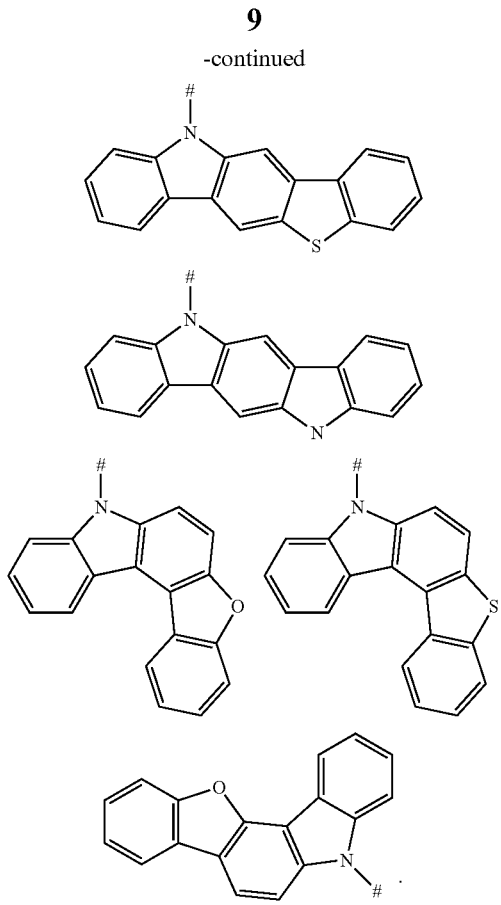

According to an embodiment of the present disclosure, D is any one of the following formulas:

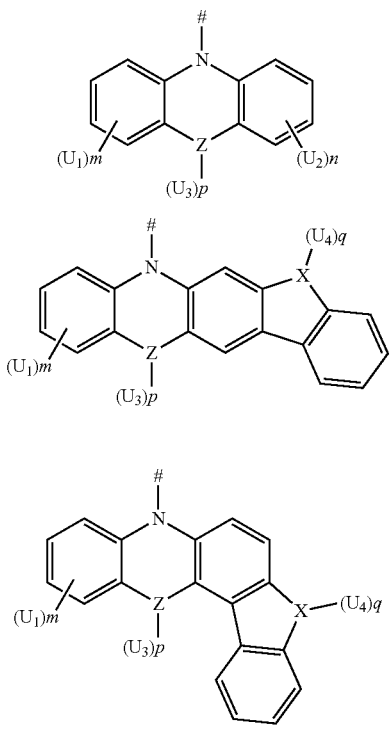

-continued

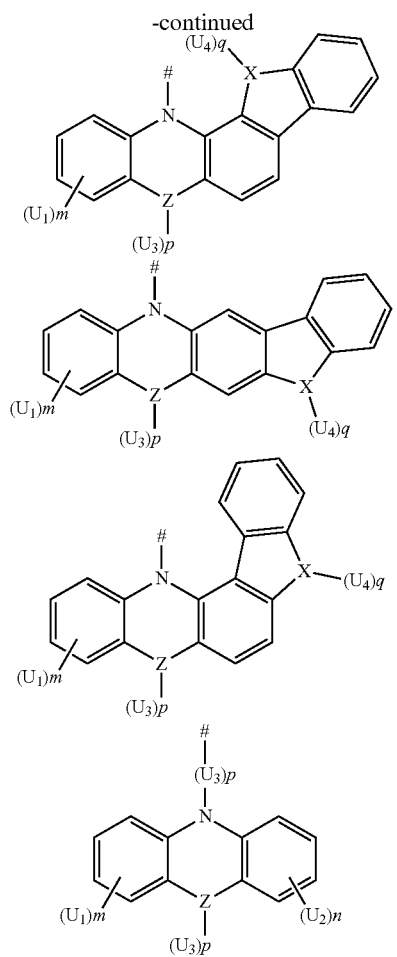

wherein Z is selected from the group consisting of a carbon atom, a nitrogen atom, oxygen atom, a sulfur atom and a silicon atom;

X is selected from the group consisting of a carbon atom, a nitrogen atom, an oxygen atom and a sulfur atom;

m, n, p and q are each an integer independently selected from 0, 1, 2 or 3;

$U_1$, $U_2$, $U_3$ and $U_4$ are each independently selected from the group consisting of a hydrogen atom, a substituted or unsubstituted C1-C30 alkyl, a substituted or unsubstituted silylene, a substituted or unsubstituted C3-C20 cycloalkyl, a substituted or unsubstituted C1-C30 alkoxy, a substituted or unsubstituted C6-C30 aryl, and a substituted or unsubstituted C10-C30 fused aryl;

when Z or X is an oxygen atom or a sulfur atom, p or q is 0; and # indicates a bonding position.

According to an embodiment of the present disclosure, D is any one of the following groups and formulas:

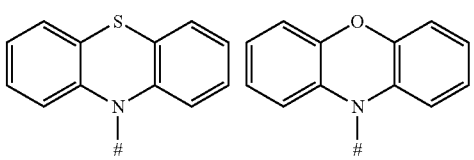

-continued

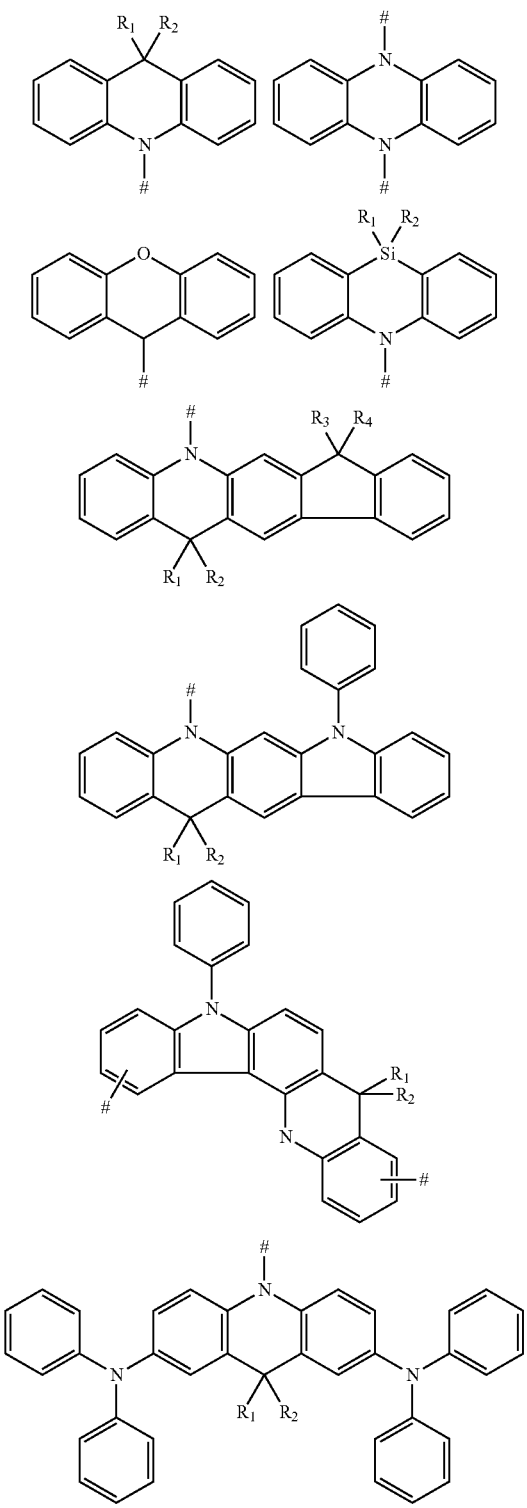

wherein $R_1$, $R_2$, $R_3$ and $R_4$ are each independently selected from the group consisting of a hydrogen atom, a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, and a substituted or unsubstituted C4-C40 heteroaryl.

According to an embodiment of the present disclosure, A is any one of the following groups:

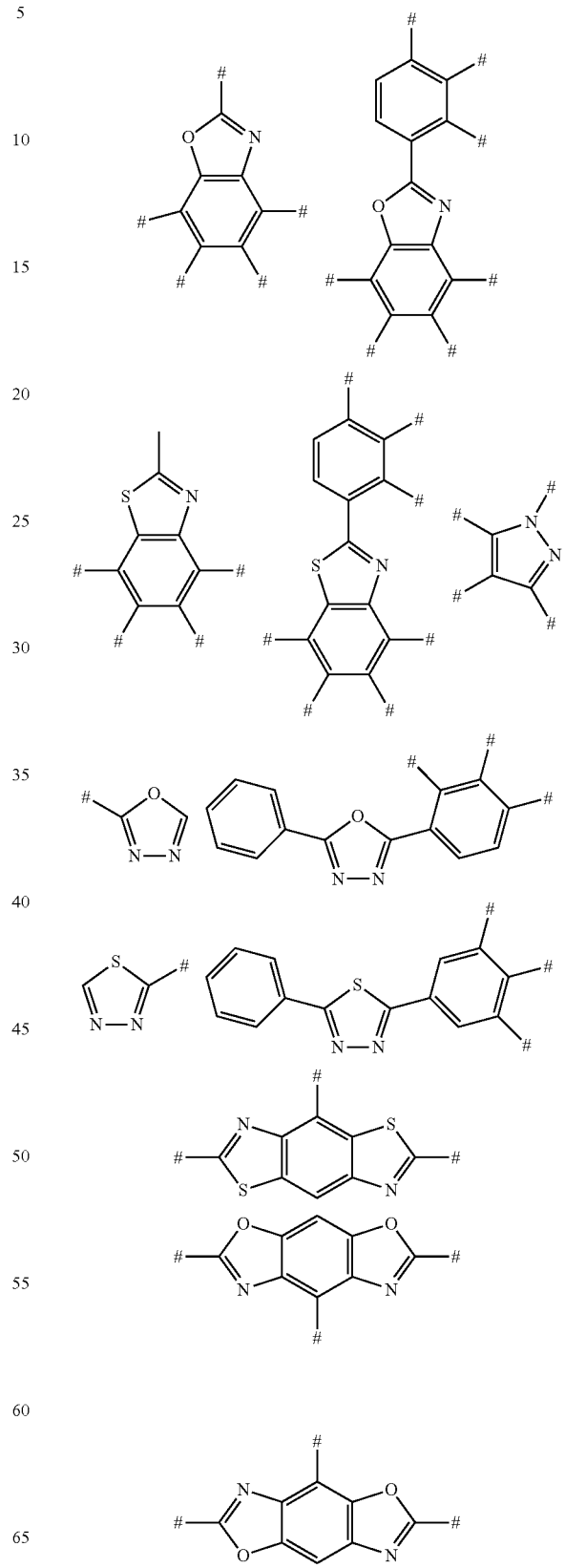

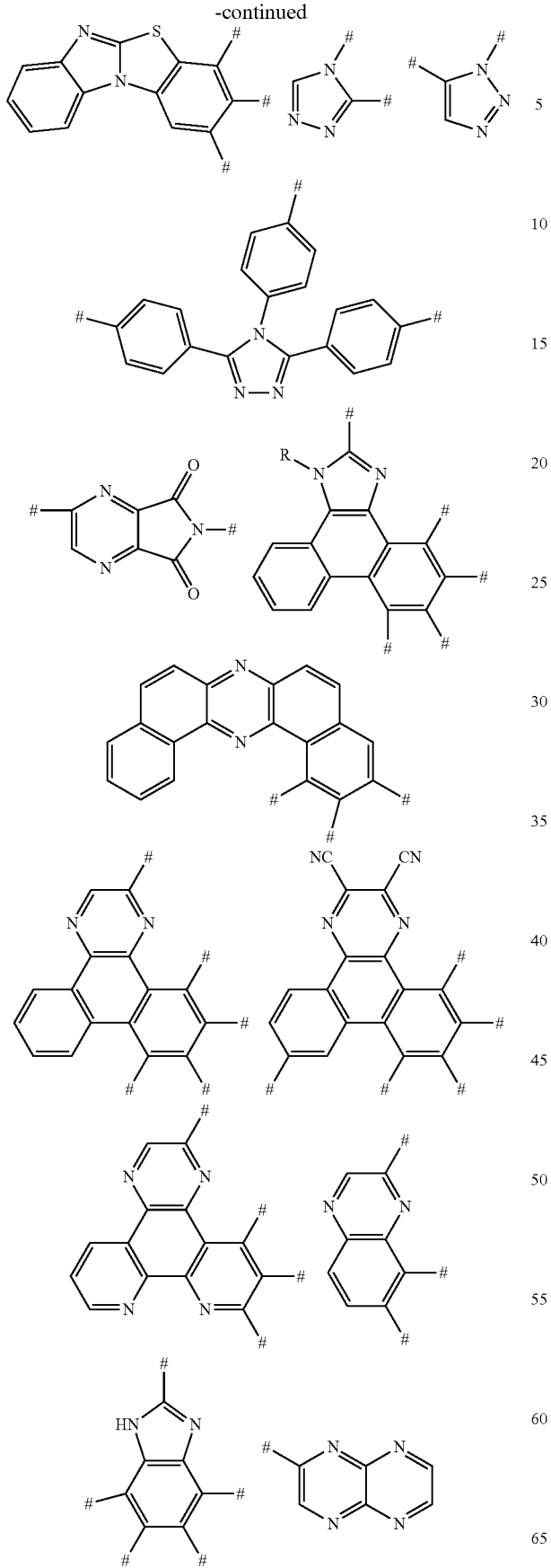
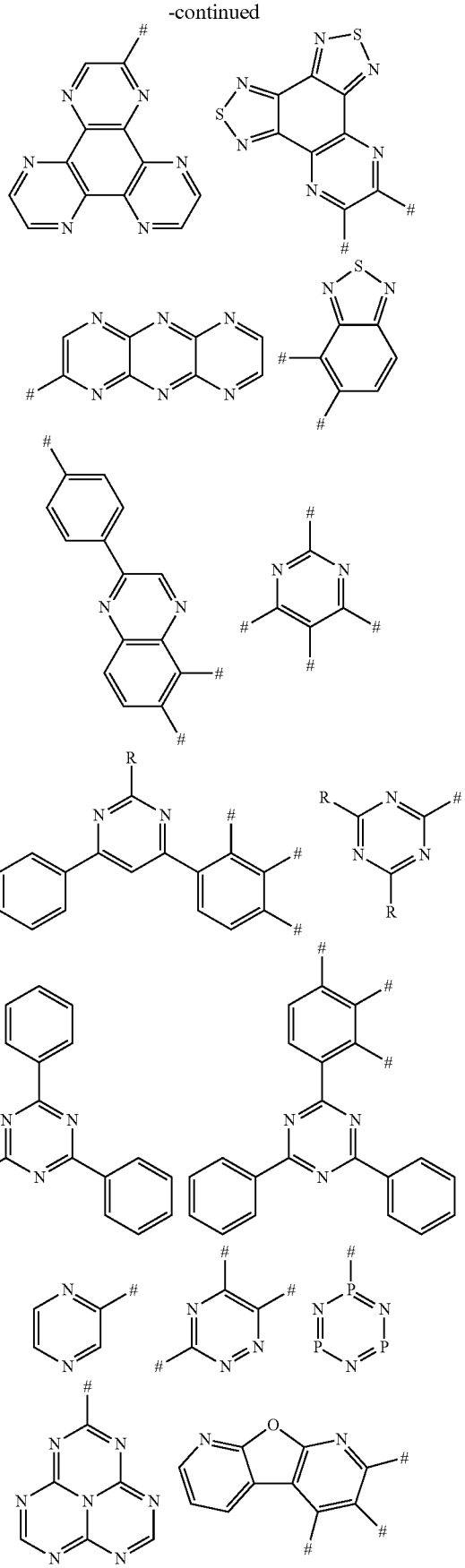

-continued

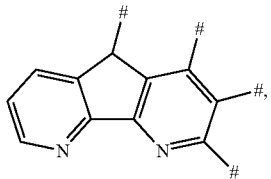

wherein R is selected from the group consisting of a hydrogen atom, C1-C20 alkyl, C1-C20 alkoxy, C4-C8 cycloalkyl, C6-C40 aryl, and C4-C40 heteroaryl; and # indicates a bonding position.

According to an embodiment of the present disclosure, A is any one of the following groups:

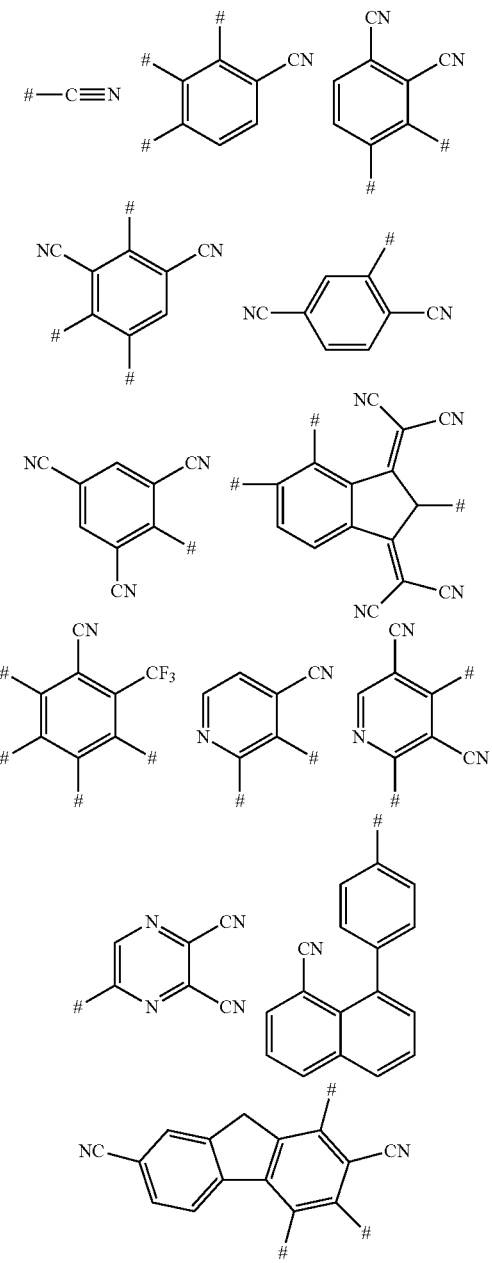

-continued

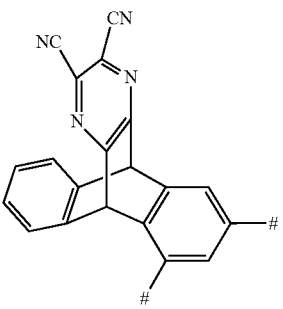

where # indicates a bonding position.

According to an embodiment of the present disclosure, A is any one of the following groups:

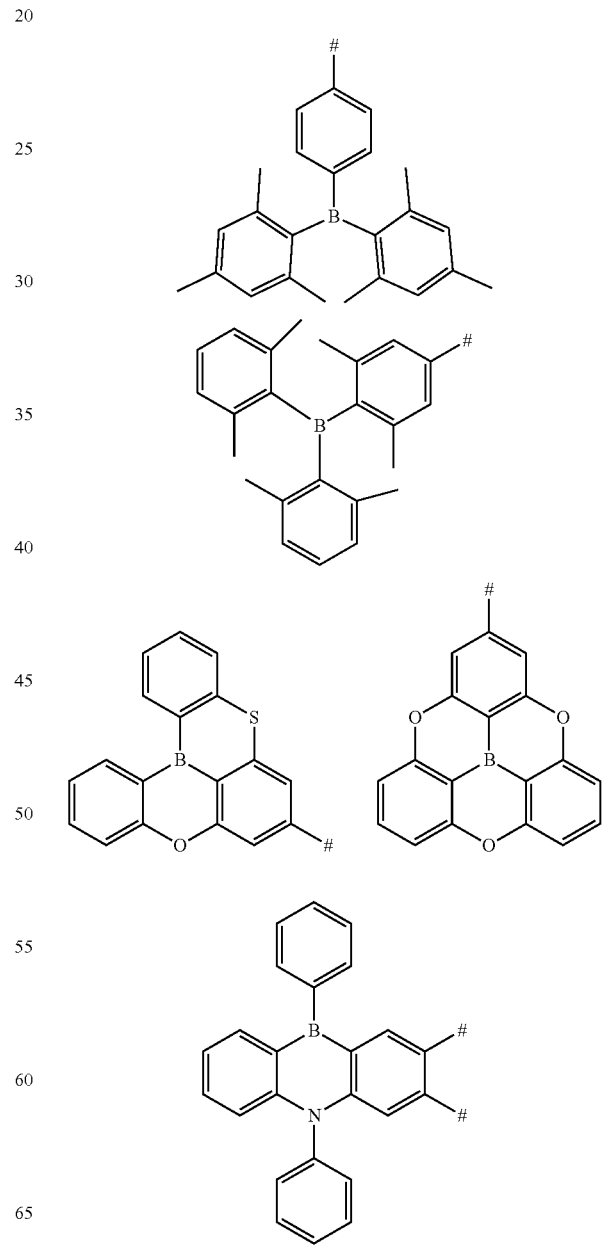

-continued
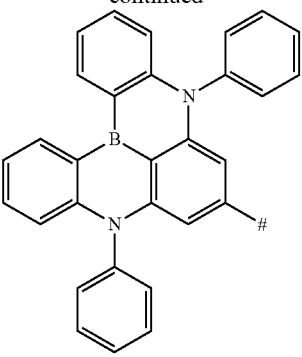
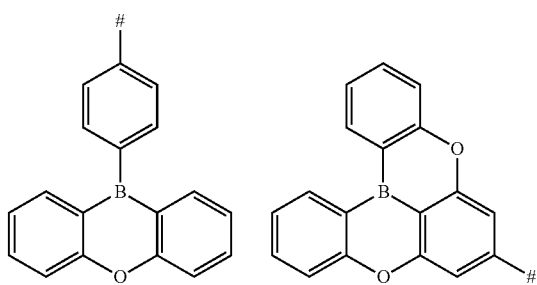
where # indicates a bonding position.
According to an embodiment of the present disclosure, A is any one of the following groups:
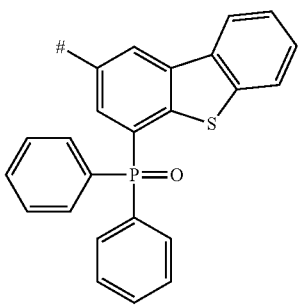
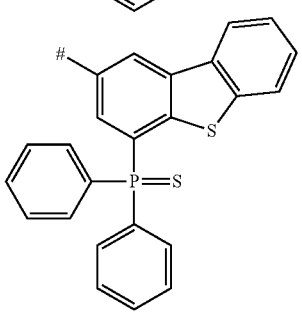
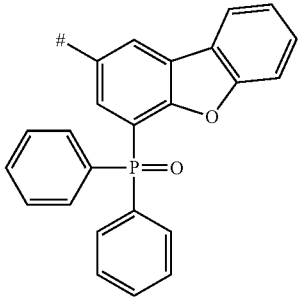
-continued
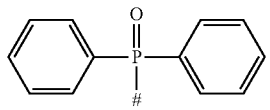
where # indicates a bonding position.
According to an embodiment of the present disclosure, the compound is any one of the following compounds:
H001
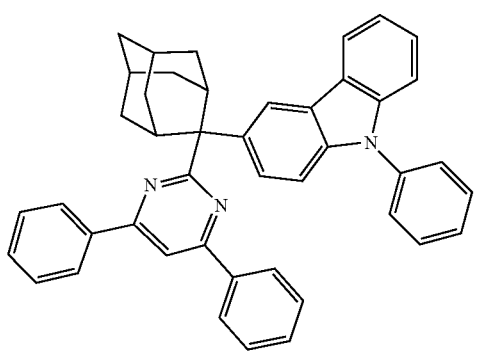
H002
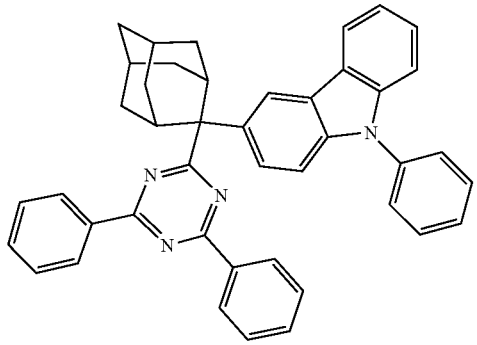
H003
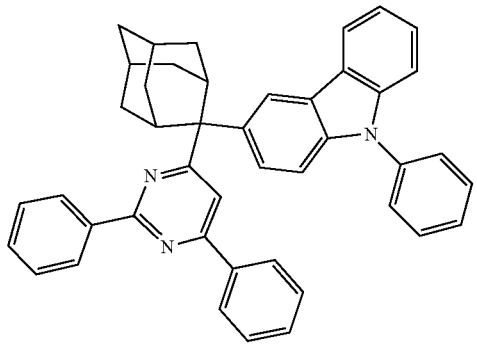

H004
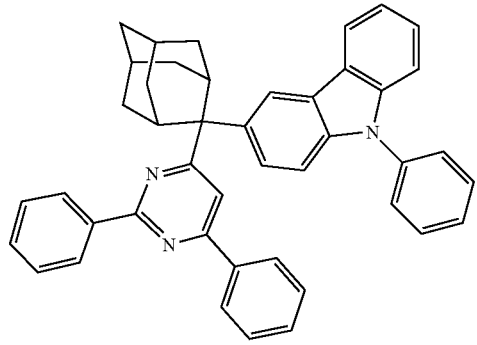
H005
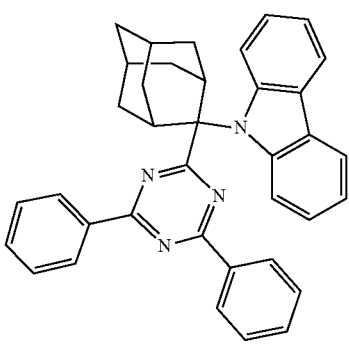
H006
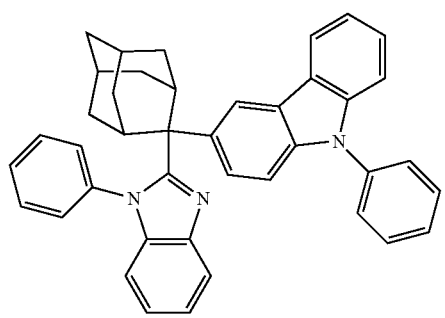
H007
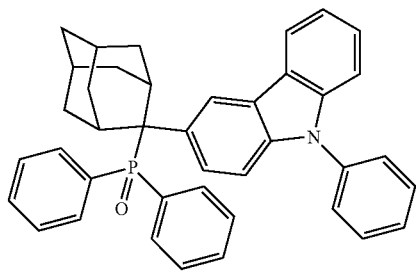
H008
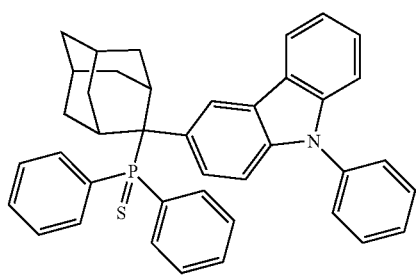
H009
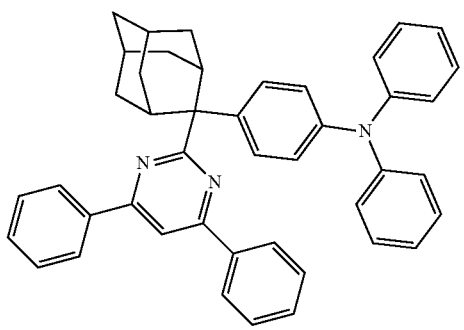
H010
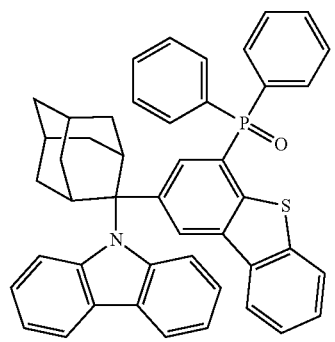
H011
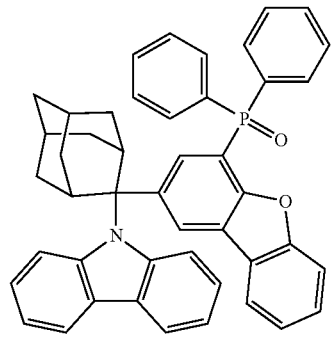
H012
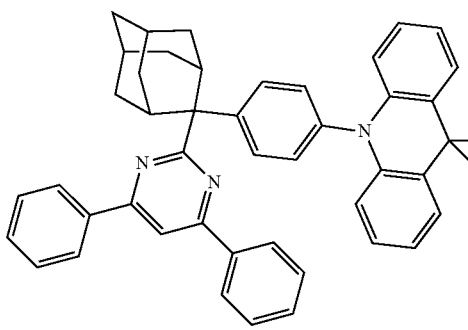
H013
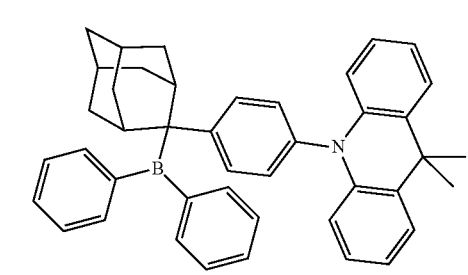

-continued
H014
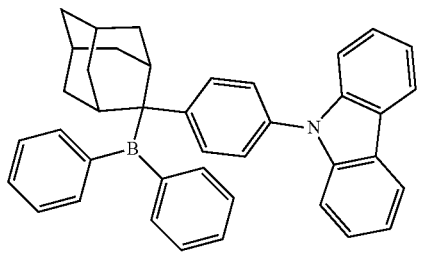
H015
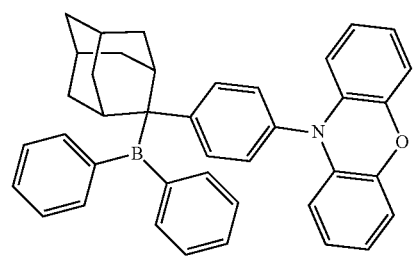
H016
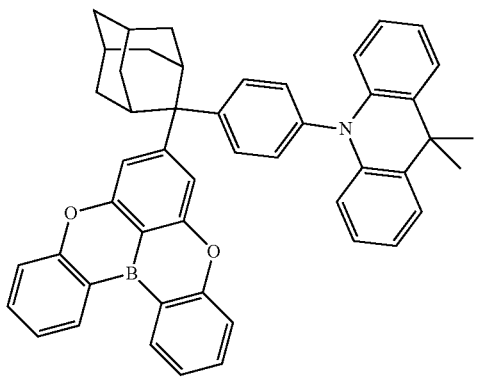
H017
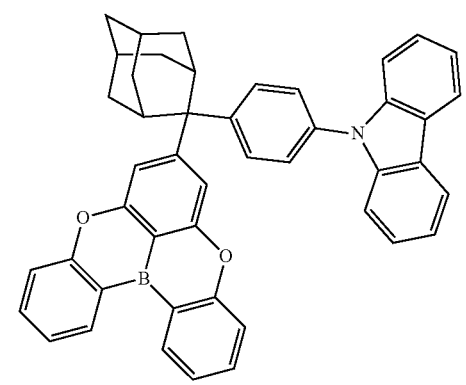
-continued
H018
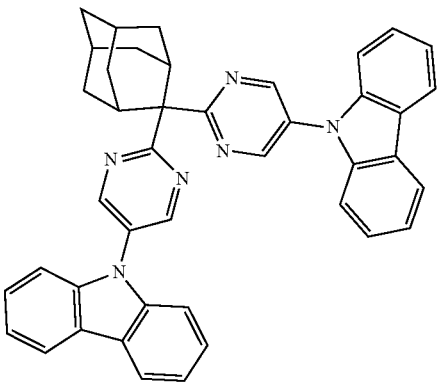
H019
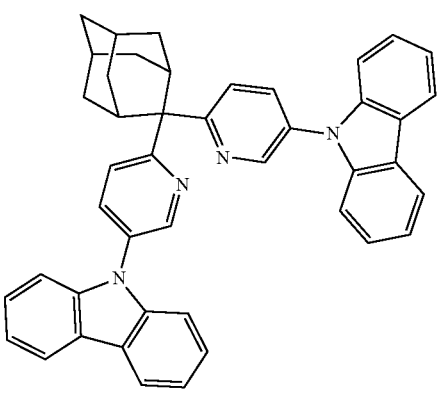
H020
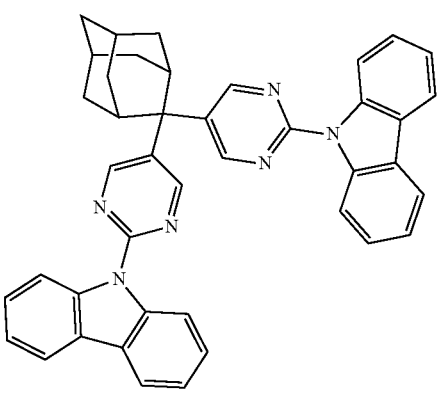
H021
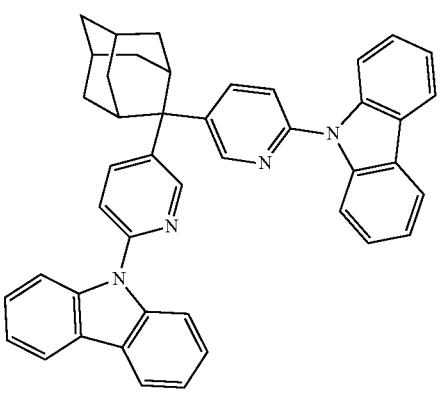

H022
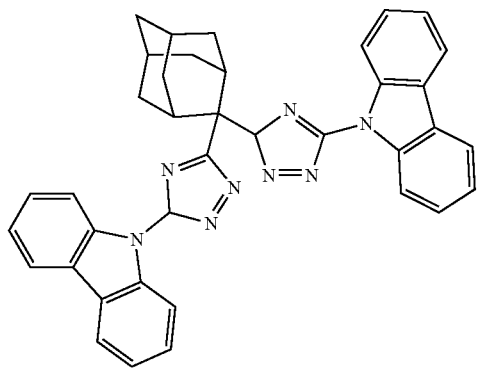
H023
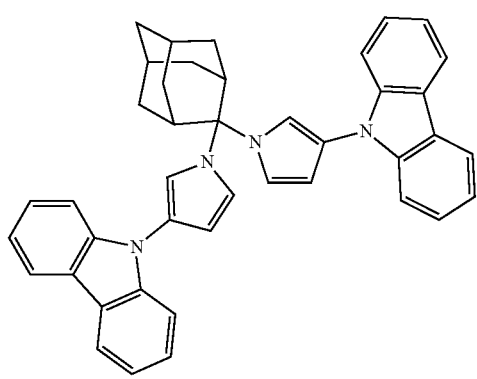
H024
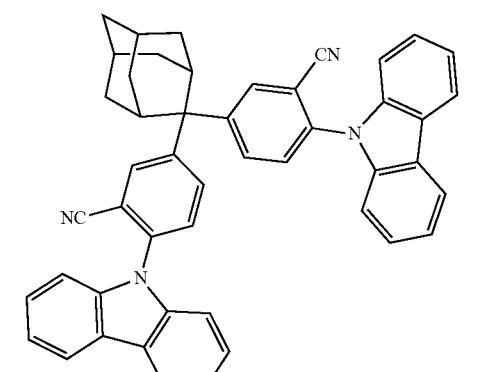
H025
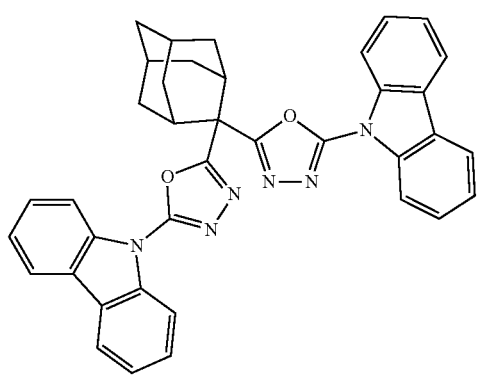
H026
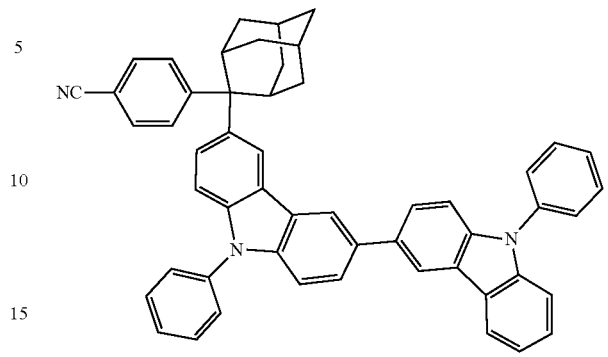
H027
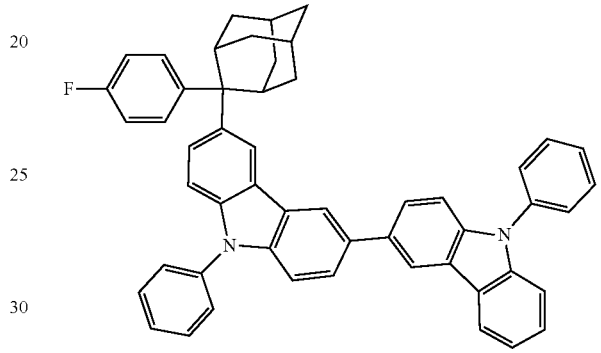
H028
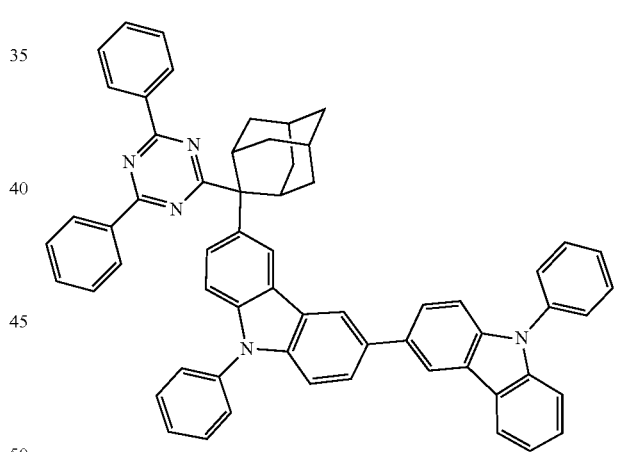
H029
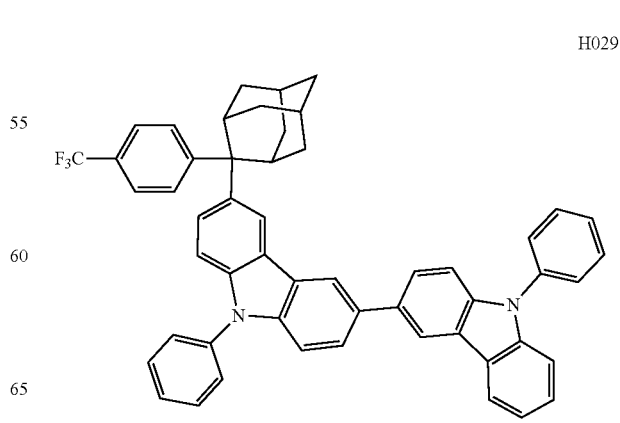

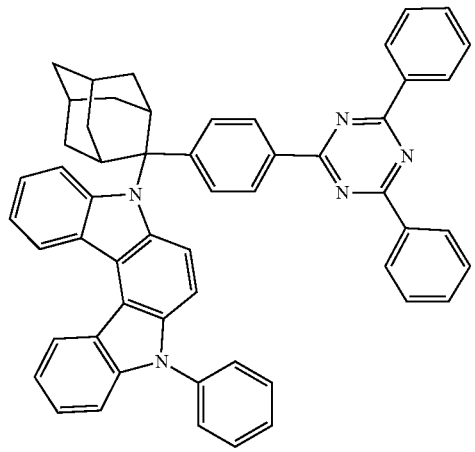
H030
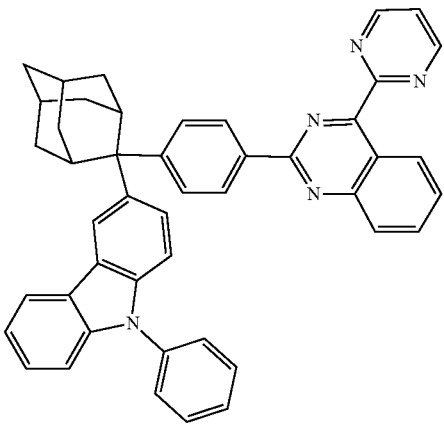
H033
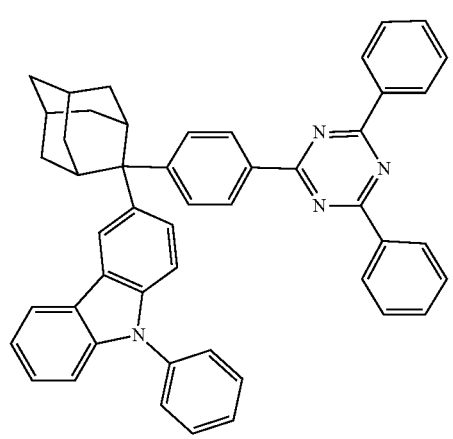
H031
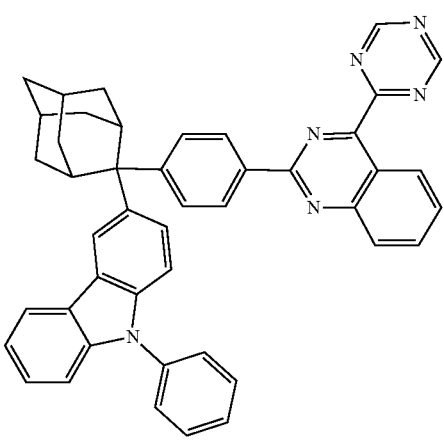
H034
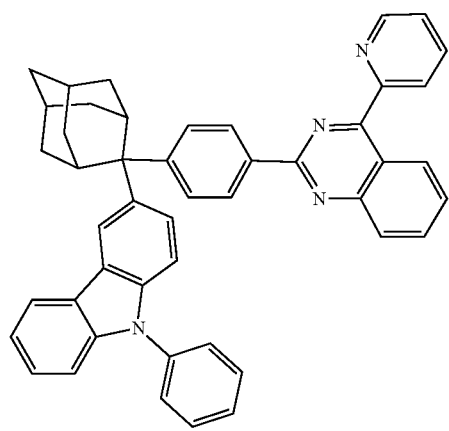
H032
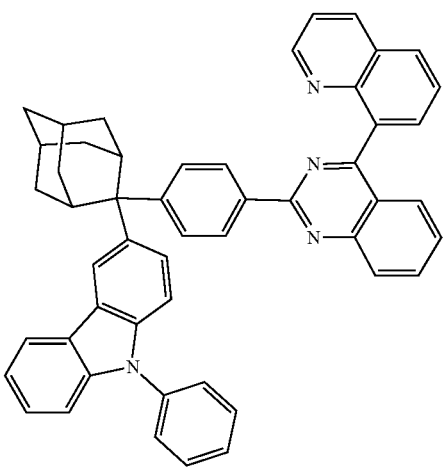
H035

H036
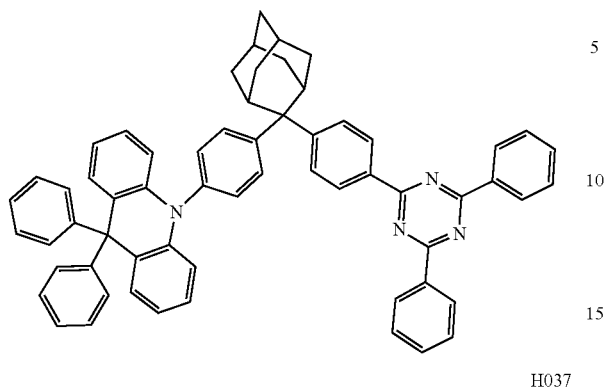
H037
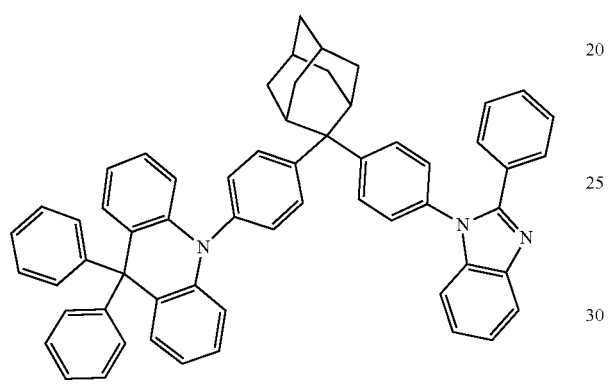
H038
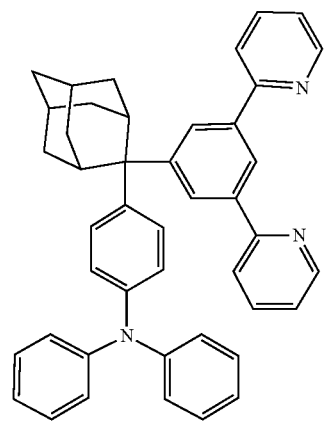
H039
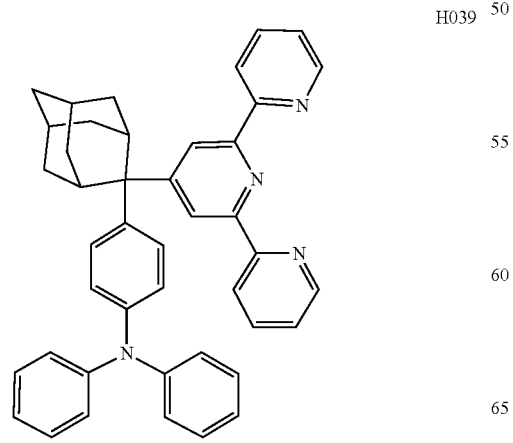
H040
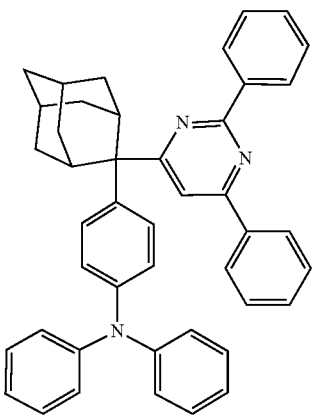
H041
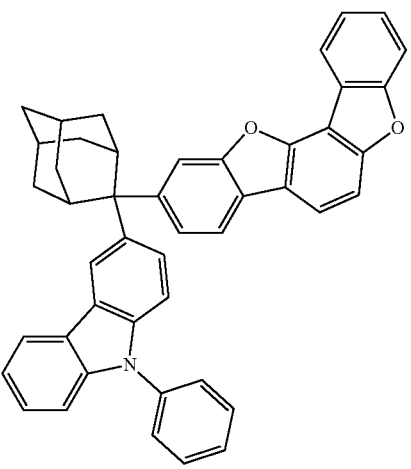
H042

H043
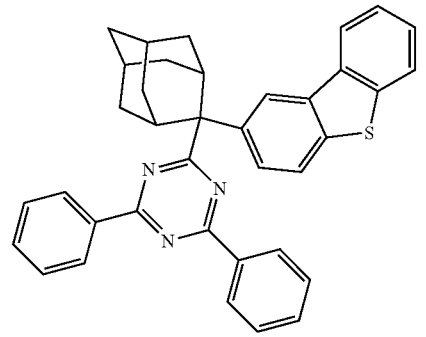
H044
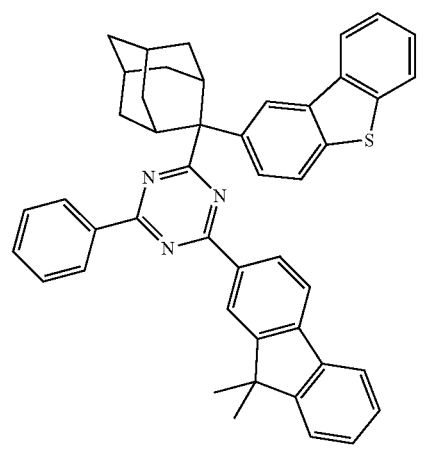
H045
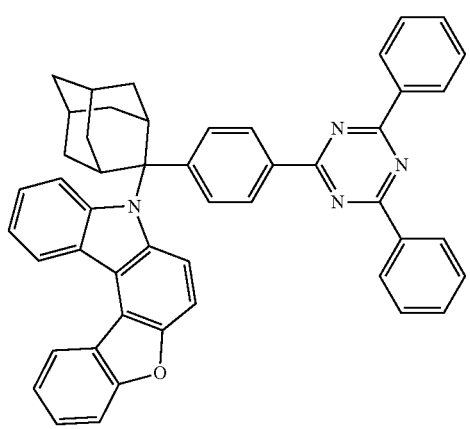
H046
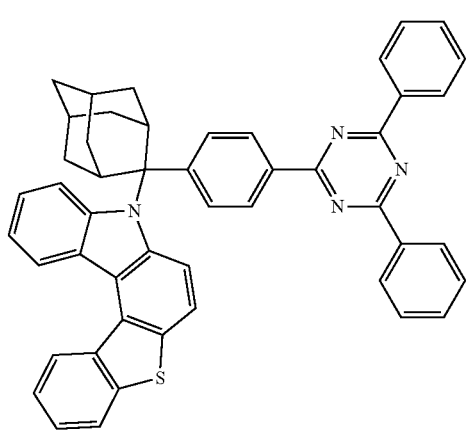
H047
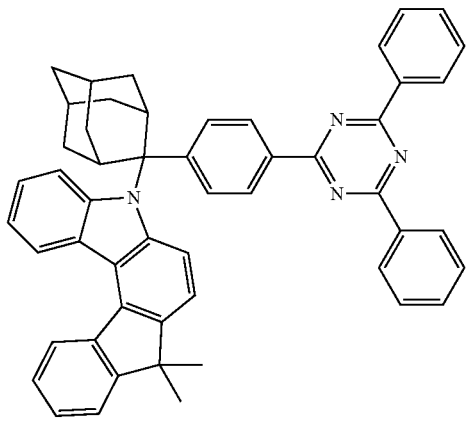
H048
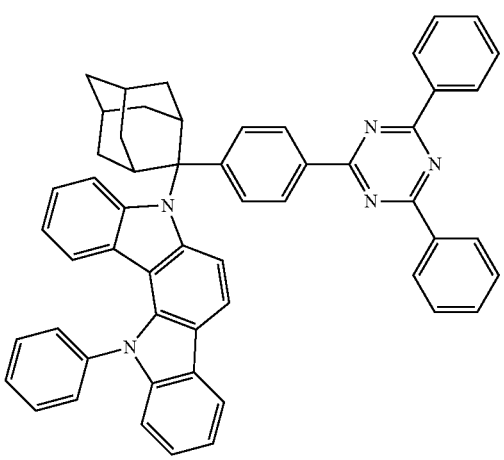
H049
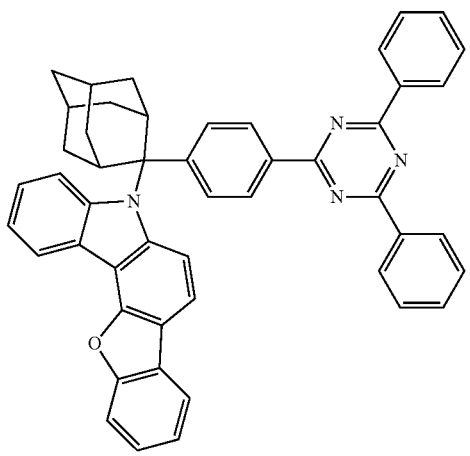

-continued
H050
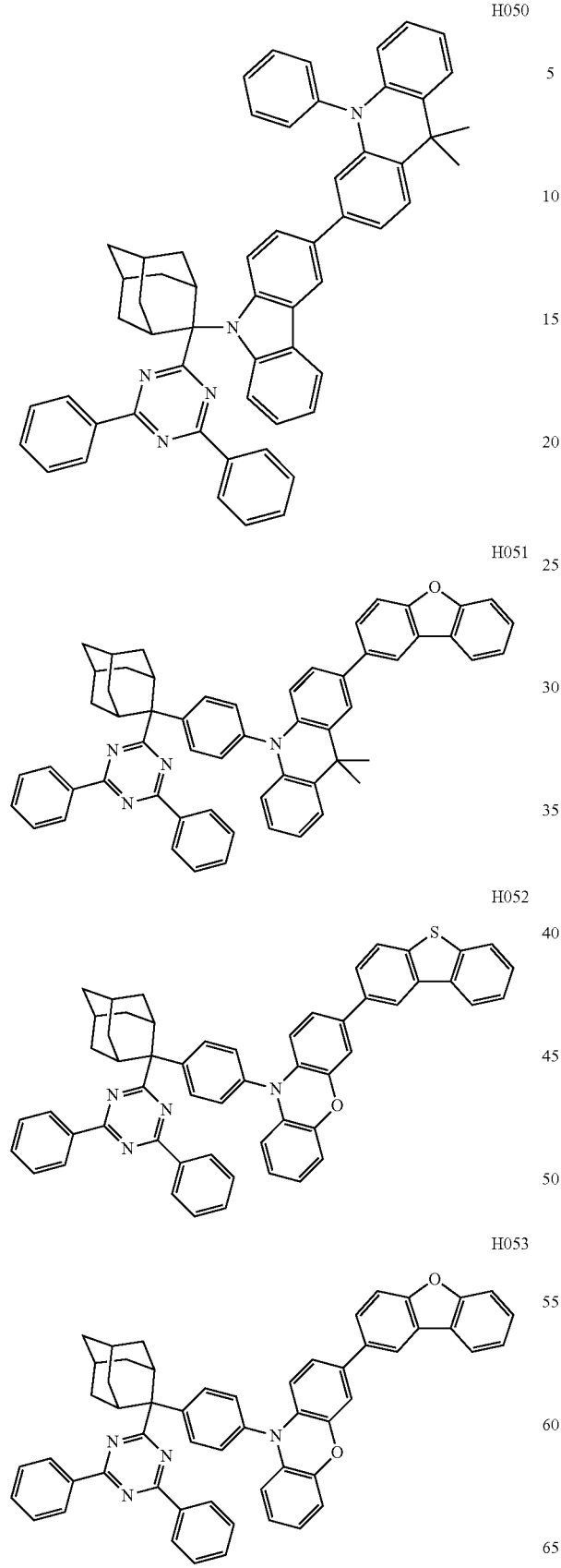
H051
H052
H053
-continued
H054
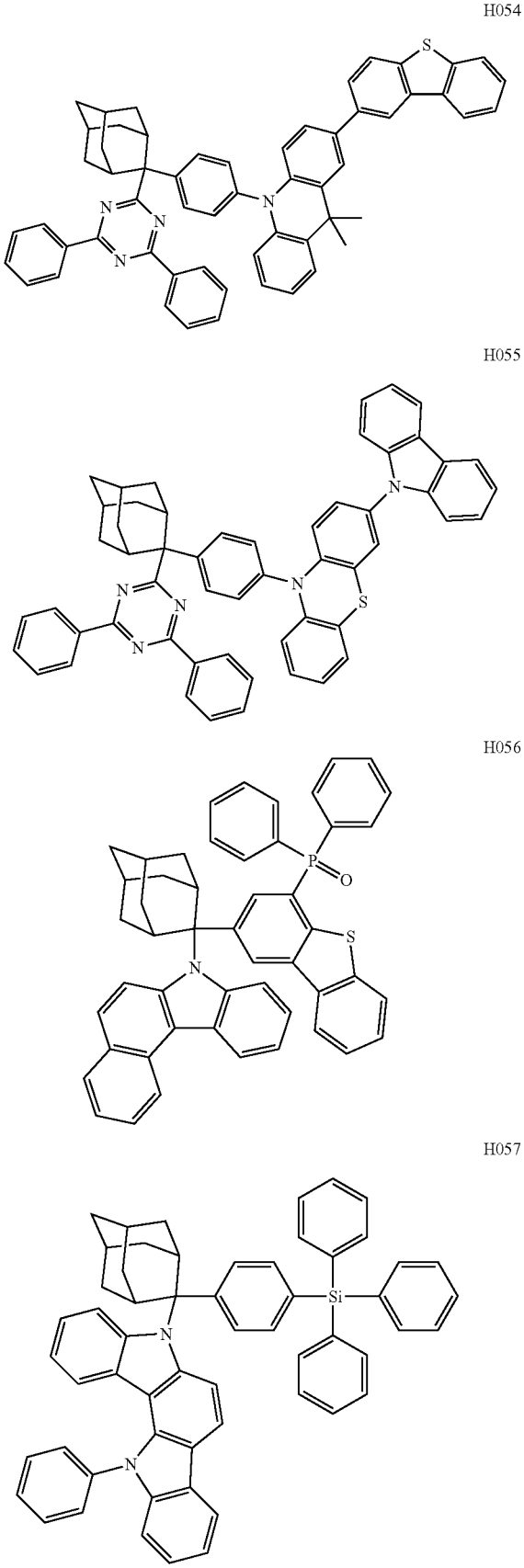
H055
H056
H057

H058
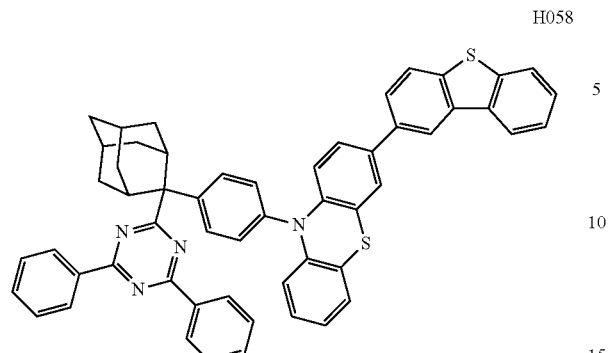
H059
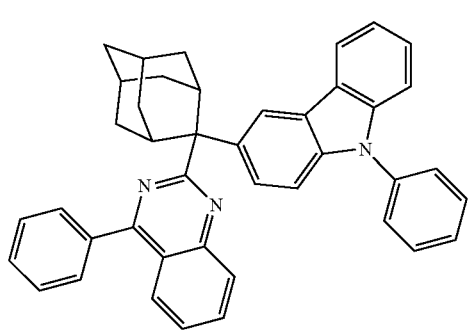
H060
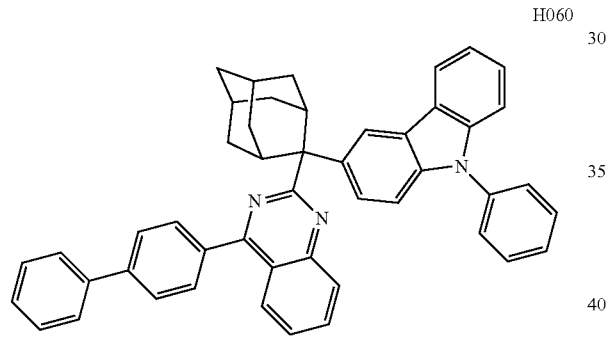
H061
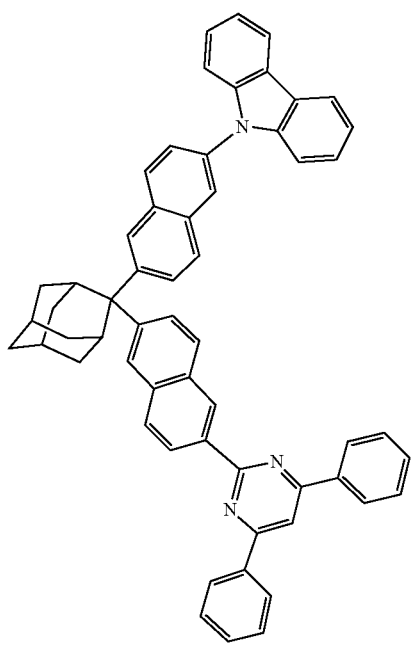
H062
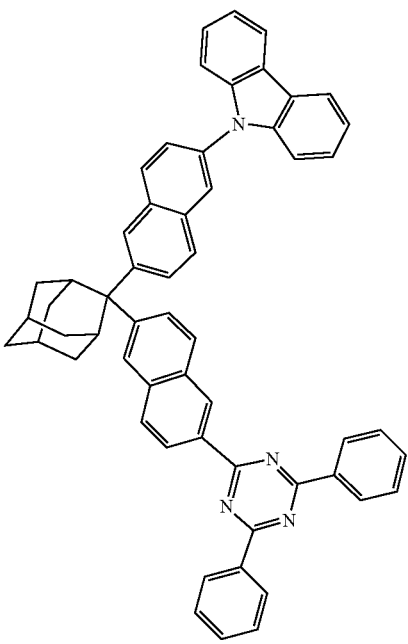
H063

-continued
H064
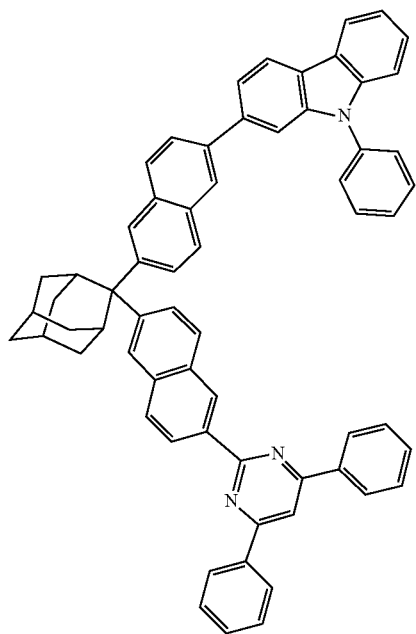
H065
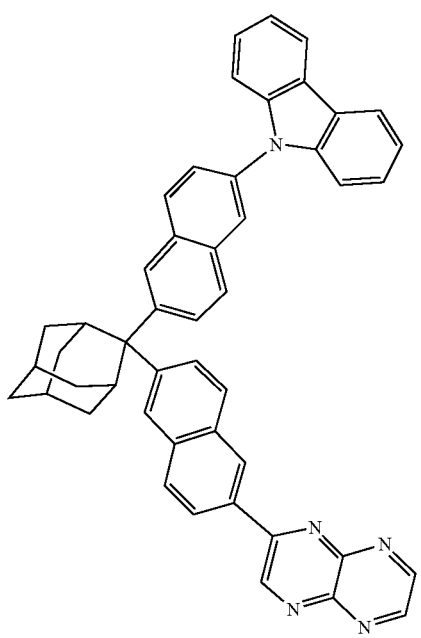
H066
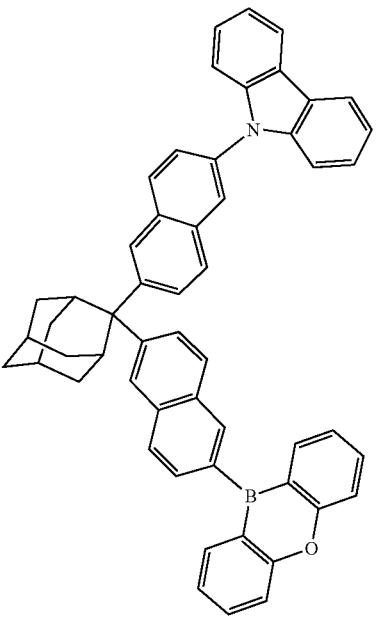
H067
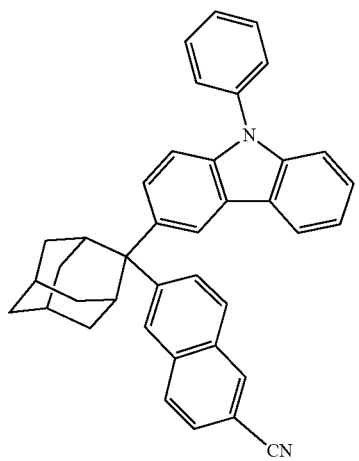
H068
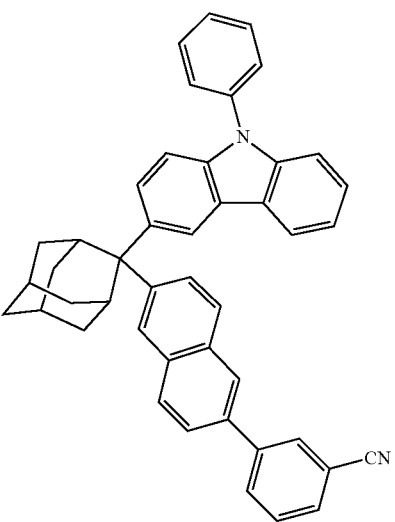

H069
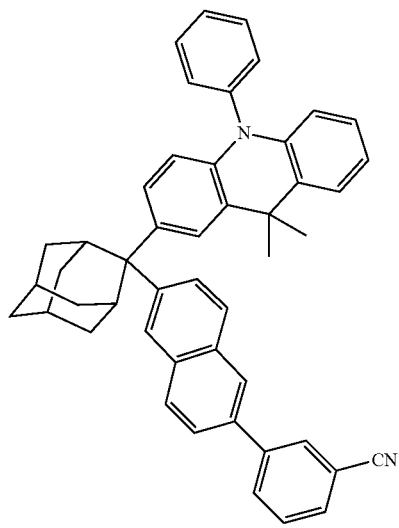
H070
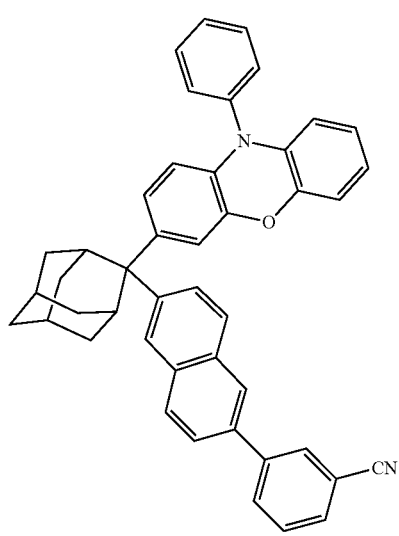
H071
H072
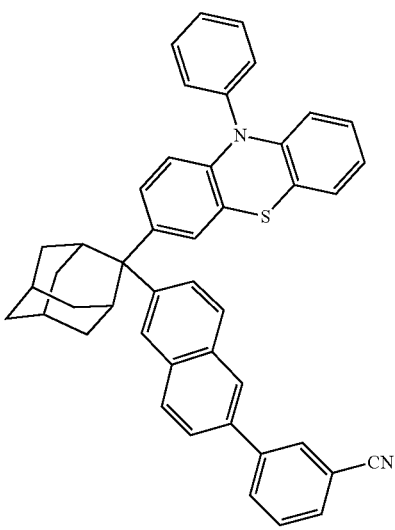
H073
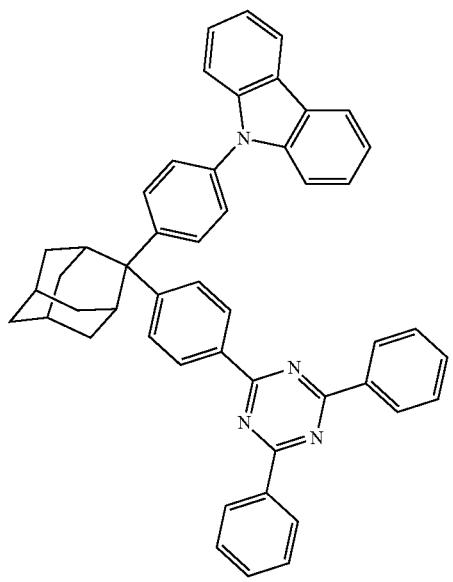

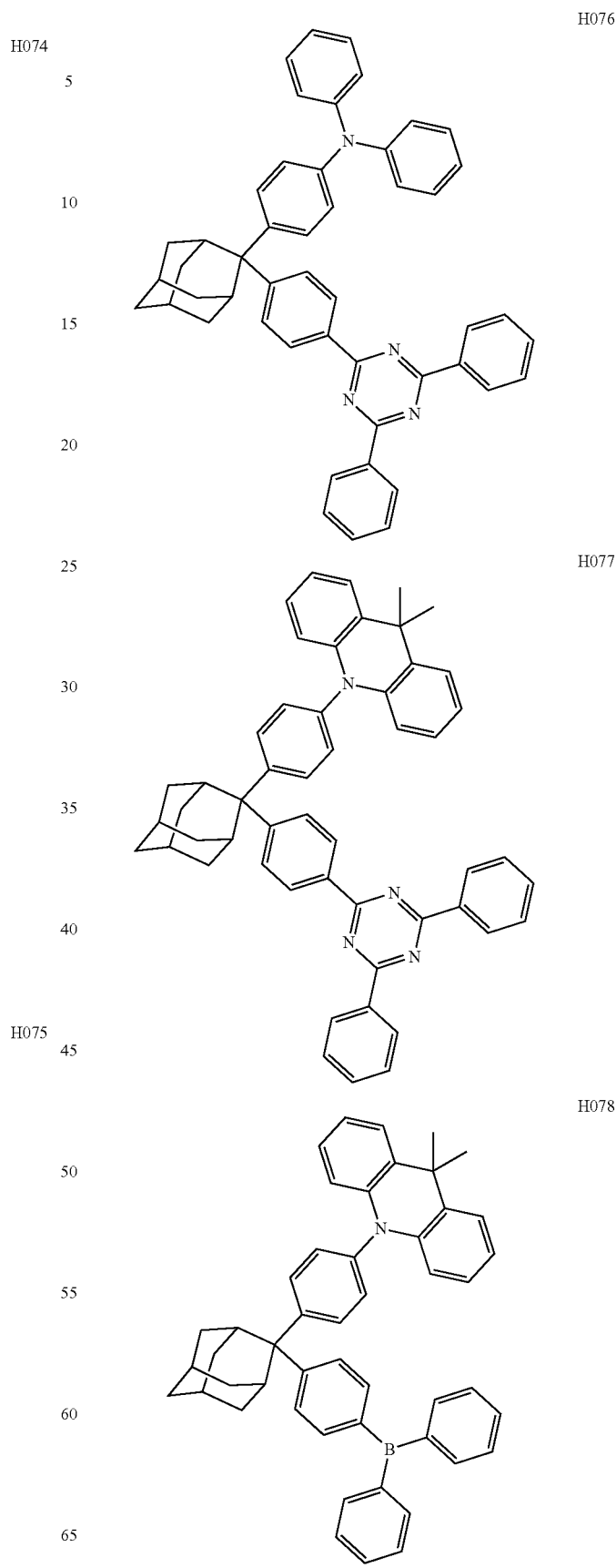

-continued

H079

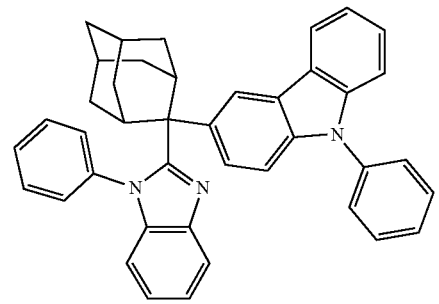

H080

H081

The compound according to the present disclosure can be used as a host material of a light-emitting layer of OLED. Accordingly, in an aspect, the present disclosure provides a display device comprising one or more compounds of the present disclosure in a host-material layer, as discussed in greater detail below.

The present disclosure provides methods for preparing four exemplary compounds H002, H018, H075 and H077, as described in the following Examples 1 to 4.

EXAMPLE 1

Synthesis of Compound H002

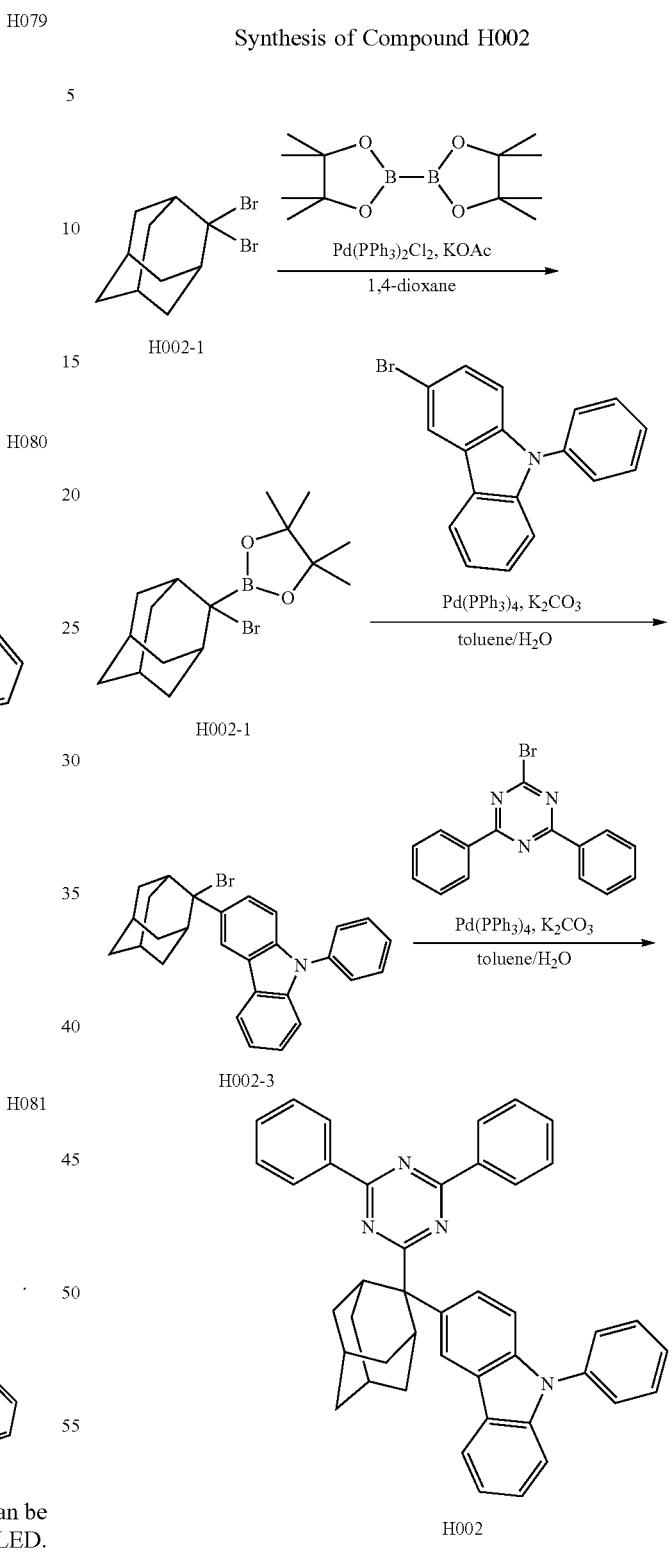

Intermediate H002-1 (15 mmol), potassium acetate (40 mmol), dried 1,4-dioxane (60 ml), Pd(PPh$_3$)$_2$Cl$_2$ (0.4 mmol) and pintanol diborate (25 mmol) were mixed in a 250 ml round-bottom flask, while stirring under nitrogen atmosphere at 90° C. for 48 h. The obtained intermediate was cooled to room temperature, added into water, and then filtered through a pad of celite. The filtrate was extracted with dichloromethane, then washed with water and dried over anhydrous magnesium sulfate. After filtering and evaporating, the raw product was purified by column chromatography on silica gel to obtain an intermediate H002-2.

H002-2 (10 mmol), 3-bromo-9-phenyl-9H-carbazole (12 mmol), Pd(PPh$_3$)$_4$ (0.3 mmol), and a mixture of toluene (30 ml)/ethanol (20 ml) and aqueous solution (10 ml) of potassium carbonate (12 mmol) were mixed in a 250 ml round-bottom flask, and refluxed to react under nitrogen atmosphere for 12 h. The obtained mixture was cooled to room temperature, added to water, and then filtered through a pad of celite. A filtrate was extracted with dichloromethane, then washed with water and dried over anhydrous magnesium sulfate. After filtering and evaporating, the raw product was purified by column chromatography on silica gel to obtain an intermediate H002-3.

H002-3 (10 mmol), 4-bromo-2,6-diphenyltriazine (12 mmol), Pd(PPh$_3$)$_4$ (0.3 mmol), and a mixture of toluene (30 ml)/ethanol (20 ml) and aqueous solution (10 ml) of potassium carbonate (12 mmol) were mixed in a 250 ml round-bottom flask, and refluxed to react under nitrogen atmosphere for 12 h. The obtained mixture was cooled to room temperature, added to water, and then filtered through a pad of celite. A filtrate was extracted with dichloromethane, then washed with water and dried over anhydrous magnesium sulfate. After filtering and evaporating, the raw product was purified by column chromatography on silica gel to obtain a final product H002.

Elemental analysis of the Compound H002: theoretical: C, 84.59; H, 6.23; N, 9.18; found: C, 84.59; H, 6.23; N, 9.18. MALDI-TOF MS: m/z C$_{43}$H$_{38}$N$_4$ calcd: 610.31, found: 610.30.

EXAMPLE 2

Synthesis of Compound H018

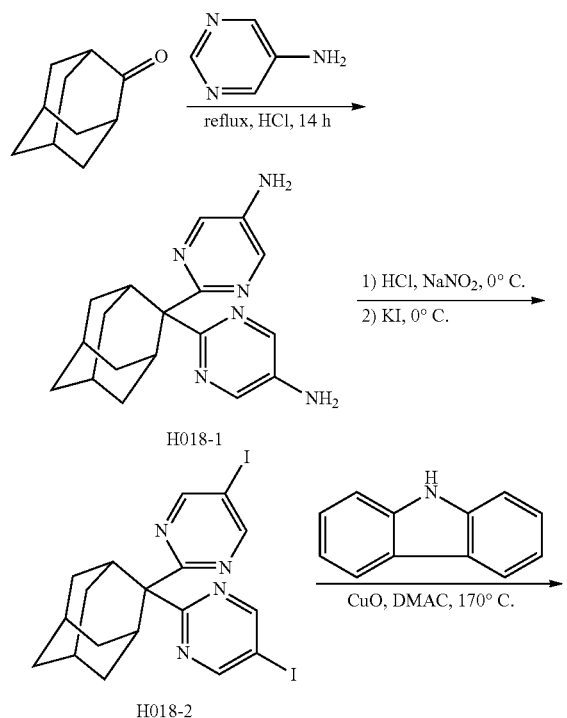

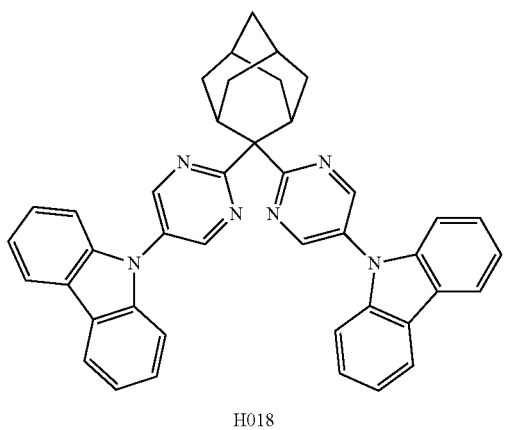

H018

2-adamantanone (15 mmol), 5-aminopyrimidine (40 mmol) and HCl (20 ml) were refluxed in a 250 ml round-bottom flask under argon atmosphere for 14 h to obtain a diaminophenyl adamantane product H018-1.

The intermediate H018-1 (15 mmol), NaNO$_2$ (40 mmol) and HCl (20 ml) were stirred at 0° C. in a 250 ml round-bottom flask under argon atmosphere for 6 h. Then, KI (40 mmol) was added, and the mixture was further stirred under argon atmosphere at 0° C. for 48 h. The obtained intermediate was added with water, and then filtered through a pad of celite. The filtrate was extracted with dichloromethane, then washed with water and dried over anhydrous magnesium sulfate. After filtering and evaporating, the raw product was purified by column chromatography on silica gel to obtain an intermediate H018-2.

The intermediate H018-2 (15 mmol), potassium acetate (80 mmol), dried 1,4-dioxane (100 ml), Pd(PPh$_3$)$_2$Cl$_2$(0.8 mmol) and pintanol diborate (50 mmol) were mixed in a 250 ml round-bottom flask under nitrogen atmosphere at 90° C. for 48 h, stirring under nitrogen atmosphere at 90° C. for 48 h. The obtained intermediate was cooled to room temperature, added to water, and then filtered through a pad of celite. The filtrate was extracted with dichloromethane, then washed with water and dried over anhydrous magnesium sulfate. After filtering and evaporating, the raw product was purified by column chromatography on silica gel to obtain a final product H018.

Elemental analysis of the Compound H018: theoretical: C, 78.75; H, 8.13; N, 13.12; found: C, 78.75; H, 8.13; N, 13.12. MALDI-TOF MS: m/z C$_{42}$H$_{52}$N$_6$ calcd: 640.43, found: 640.42.

EXAMPLE 3

Synthesis of Intermediate H075-1

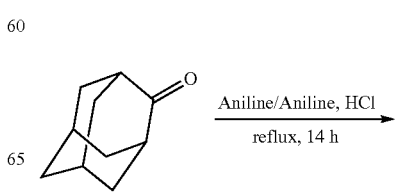

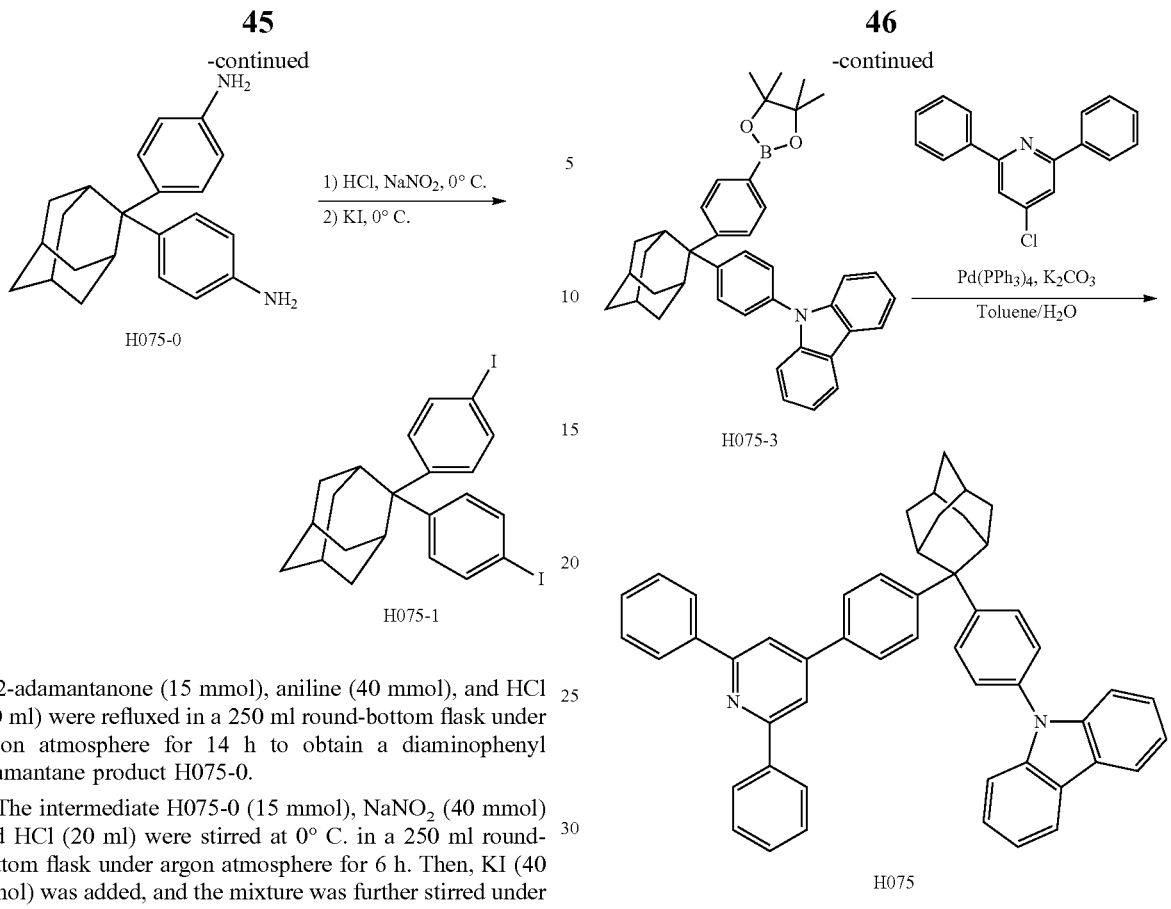

2-adamantanone (15 mmol), aniline (40 mmol), and HCl (20 ml) were refluxed in a 250 ml round-bottom flask under argon atmosphere for 14 h to obtain a diaminophenyl adamantane product H075-0.

The intermediate H075-0 (15 mmol), NaNO$_2$ (40 mmol) and HCl (20 ml) were stirred at 0° C. in a 250 ml round-bottom flask under argon atmosphere for 6 h. Then, KI (40 mmol) was added, and the mixture was further stirred under argon atmosphere at 0° C. for 48 h. The obtained intermediate was added with water, and then filtered through a pad of celite. The filtrate was extracted with dichloromethane, then washed with water and dried over anhydrous magnesium sulfate. After filtering and evaporating, the raw product was purified by column chromatography on silica gel to obtain an intermediate H075-1.

Synthesis of Compound H075

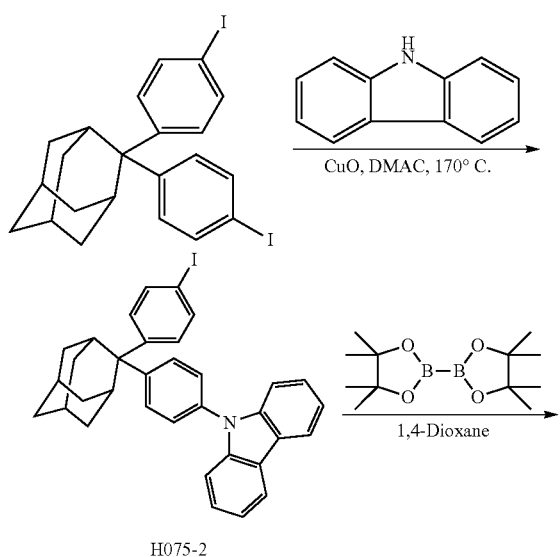

2,2-bis(4-iodo-phenyl)-adamantane (15 mmol), cuprous oxide (40 mmol), DMAC (20 ml) were refluxed in a 250 ml round-bottom flask under argon atmosphere for 48 h. The obtained intermediate was cooled to room temperature, added with water, and then filtered through a pad of celite. The filtrate was extracted with dichloromethane, then washed with water and dried over anhydrous magnesium sulfate. After filtering and evaporating, the raw product was purified by column chromatography on silica gel to obtain an intermediate H075-2.

Intermediate H075-2 (15 mmol) and potassium acetate (40 mmol) were mixed with dried 1,4-dioxane (60 ml), Pd(PPh$_3$)$_2$Cl$_2$ (0.4 mmol) and pintanol diborate (25 mmol) in a 250 ml round-bottom flask, stirring under nitrogen atmosphere at 90° C. for 48 h. The obtained intermediate was cooled to room temperature, added to water, and then filtered through a pad of celite. A filtrate was extracted with dichloromethane, then washed with water and dried over anhydrous magnesium sulfate. After filtering and evaporating, the raw product was purified by column chromatography on silica gel to obtain an intermediate H075-3.

H075-3 (10 mmol), 2-chloro-4,6-diphenyl-1,3,5-triazine (12 mmol) and Pd(PPh$_3$)$_4$ (0.3 mmol), and a mixture of toluene (30 ml)/ethanol (20 ml) and aqueous solution (10 ml) of potassium carbonate (12 mmol) were added in a 250 ml round-bottom flask, and refluxed to react under nitrogen atmosphere for 12 h. The obtained mixture was cooled to room temperature, added with water, and then filtered through a pad of celite. The filtrate was extracted with dichloromethane, then washed with water and dried over anhydrous magnesium sulfate. After filtering and evaporating, the raw product was purified by column chromatography on silica gel to obtain a final product H075.

Elemental analysis of the Compound H075: theoretical: C, 89.70; H, 6.16; N, 4.14; found: C, 89.70; H, 6.15; N, 64.15. MALDI-TOF MS: m/z $C_{51}H_{42}N_2$ calcd: 682.3, found: 682.2.

EXAMPLE 4

Synthesis of Compound H077

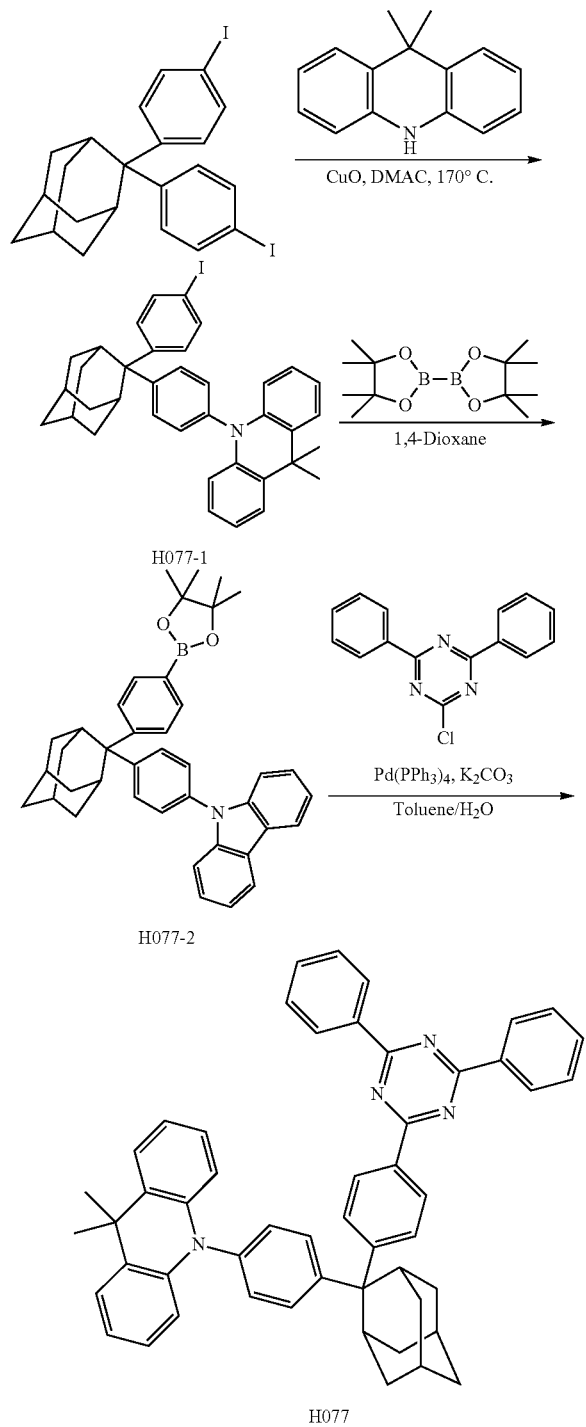

2,2-bis(4-iodo-phenyl)-adamantane (15 mmol), 9,9-dimethyl-9,10-dihydroacridine (20 mmol), cuprous oxide (40 mmol) and DMAC (20 ml) were refluxed in a 250 ml round-bottom flask under argon atmosphere for 48 h. The obtained intermediate was cooled to room temperature, added with water and then filtered through a pad of celite. The filtrate was extracted with dichloromethane, then washed with water and dried over anhydrous magnesium sulfate. After filtering and evaporating, the raw product was purified by column chromatography on silica gel to obtain an intermediate H077-1.

Intermediate H077-1 (15 mmol), potassium acetate (40 mmol), dried 1,4-dioxane (60 ml), $Pd(PPh_3)_2Cl_2$ (0.4 mmol) and pintanol diborate (25 mmol) were mixed in a 250 ml round-bottom flask, stirring under nitrogen atmosphere at 90° C. for 48 h. The obtained intermediate was cooled to room temperature, added to water, and then filtered through a pad of celite. The filtrate was extracted with dichloromethane, then washed with water and dried over anhydrous magnesium sulfate. After filtering and evaporating, the raw product was purified by column chromatography on silica gel to obtain an intermediate H077-2.

H077-2 (10 mmol), 2-chloro-4,6-diphenyl-1,3,5-triazine (12 mmol) and $Pd(PPh_3)_4$ (0.3, and a mixture of toluene (30 ml)/ethanol (20 ml) and aqueous solution (10 ml) of potassium carbonate (12 mmol) were mixed in a 250 ml round-bottom flask, and refluxed to react under nitrogen atmosphere for 12 h. The obtained mixture was cooled to room temperature, added to water, and then filtered through a pad of celite. The filtrate was extracted with dichloromethane, then washed with water and dried over anhydrous magnesium sulfate. After filtering and evaporating, the raw product was purified by column chromatography on silica gel to obtain a final product H077.

Elemental analysis of the Compound H077: theoretical: C, 77.70; H, 15.33; N, 6.97; found: C, 77.70; H, 15.33; N, 6.97. MALDI-TOF MS: m/z $C_{52}H_{123}N_4$ calcd: 803.97, found: 803.96.

Compound Performance Tests (1) Simulation Calculation of the Compounds

With respect to Compounds H002, H018, H075 and H077, the distribution of the molecular frontier orbitals was optimized and calculated by applying a density functional theory (DFT) and using a Gaussian 09 software with $B_3LYP/6-31G(d)$ calculation level. Meanwhile, the singlet energy level S1 and triplet energy level T1 of each of the compounds H002, H018, H075 and H077 were simulated by applying time-dependent density functional theoretical (TD-DFT). The results are listed in Table 1, in which $E_g$=HOMO-LUMO, the values of $E_g$ are absolute values.

TABLE 1

Energy levels of exemplary compounds

| Compound | HOMO(eV) | LUMO(eV) | Eg(eV) | $E_T$(eV) |
|---|---|---|---|---|
| H002 | −5.276 | −1.752 | 3.524 | 3.0217 |
| H018 | −5.575 | −1.465 | 4.110 | 3.1603 |
| H075 | −5.257 | −1.840 | 3.417 | 2.9840 |
| H077 | −5.248 | −0.727 | 4.521 | 3.1482 |

As can be seen from Table 1, H002, H018, H075 and H077, as the host materials, have moderate HOMO and LUMO energy levels and high triplet state $E_T$ (>2.85 ev), which is suitable to be used as red light material ($E_T$>2.2) Ev), green light material ($E_T$>2.5 ev) and blue light material ($E_T$>2.7 ev), achieving the energy transfer between the host material and the guest material and preventing backflow of charges.

The present disclosure also provides a display panel. The display panel includes an organic light-emitting device. The organic light-emitting device includes an anode, a cathode arranged opposite to the anode, and a light-emitting layer disposed between the anode and the cathode. The light-emitting layer includes a host material and a guest material. The host material of the light-emitting layer is one or more of the compounds described above.

According to an embodiment of the display panel of the present disclosure, the light-emitting layer is a blue light-emitting layer, and the host material is a host material of a blue light-emitting layer.

According to an embodiment of the display panel of the present disclosure, the light-emitting layer is a green light-emitting layer, and the host material is a host material of a green light-emitting layer.

According to an embodiment of the display panel of the present disclosure, the host material has a higher singlet energy level S1 than the guest material, and a difference between the singlet energy level S1 of the host material and the singlet energy level S1 of the guest material is less than 0.8 eV; the host material has a higher triplet energy level T1 than the guest material, and a difference between the triplet energy level T1 of the host material and the triplet energy level T1 of the guest material is less than 0.4 eV.

According to an embodiment of the display panel of the present disclosure, the organic light-emitting device further includes one or more layers of a hole injection layer, a hole transmission layer, an electron blocking layer, a hole blocking layer, an electron transmission layer or an electron injection layer.

The present disclosure also provides a display panel. In an embodiment, the display panel includes an organic light-emitting device. In an embodiment, the organic light-emitting device includes an anode, a cathode arranged opposite to the anode, a capping layer disposed at a side of the cathode facing away from the anode, and an organic layer disposed between the anode and the cathode. In an embodiment, the organic layer includes an electron transmission layer, a hole transmission layer, and a light-emitting layer. In an embodiment, at least one of the capping layer, the electron transmission layer, the hole transmission layer, and the light-emitting layer is comprises a compound of the present disclosure.

In an embodiment of the display panel provided by the present disclosure, the anode of the organic light-emitting device comprises a metal, such as a metal selected from the group consisting of copper, gold, silver, iron, chromium, nickel, manganese, palladium, platinum, and alloys thereof. In an embodiment, the anode comprises a metal oxide, such as a metal oxide selected from the group consisting of indium oxide, zinc oxide, indium tin oxide (ITO), indium zinc oxide (IZO), and combinations thereof. In an embodiment, the anode comprises a conductive polymer, such as a conductive polymer selected from the group consisting of polyaniline, polypyrrole, poly(3-methylthiophene), and combinations thereof. In addition to the anode materials mentioned above, in an embodiment, the anode can also be made of any suitable material known in the related art, or combinations thereof, as long as the material is conductive to the hole injection.

In the display panel provided by the present disclosure, in an embodiment, the cathode of the organic light-emitting device comprises a metal, such as a metal selected from the group consisting of aluminum, magnesium, silver, indium, tin, titanium, and alloys thereof. In an embodiment, the cathode also comprises a multiple-layered metal material, such as a multiple-layered material selected from the group consisting of LiF/Al, $LiO_2$/Al, $BaF_2$/Al, and combinations thereof. In addition to the cathode materials listed above, the cathode also can be made of any suitable material known in the related art, or combinations thereof, as long as the material of the cathode is conductive to hole injection.

The organic light-emitting device can be manufactured according to methods well known in the art, which will not be elaborated herein. In the present disclosure, the organic light-emitting device can be manufactured by the following steps: forming an anode on a transparent or opaque smooth substrate; forming an organic thin layer on the anode; and further forming a cathode on the organic thin layer. The organic thin layer can be formed with a known method such as vapor deposition, sputtering, spin coating, dipping, ion plating, and the like.

Exemplary Device Examples are provided below to illustrate the practical application of the compounds of the present disclosure in the organic light-emitting display panel.

Device Example 1

Figure 3:
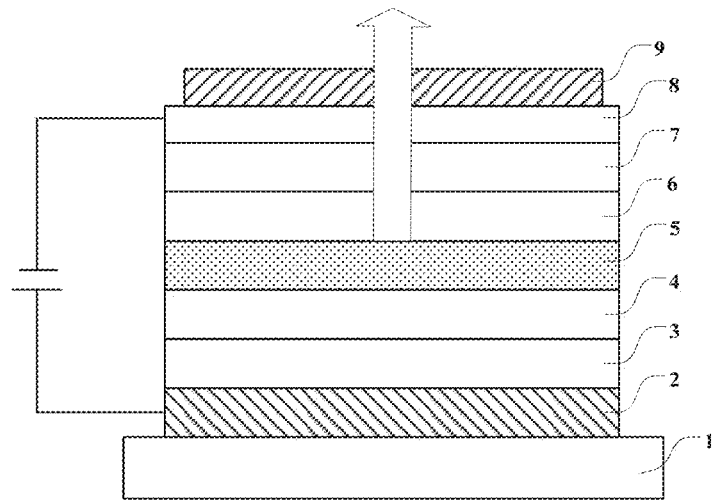
FIG. 3 is a structural schematic diagram of an OLED according to an embodiment of the present disclosure.

This example provides an organic light-emitting device. As shown in FIG. 3, the organic light-emitting device includes: a glass substrate 1, an ITO anode 2, a first hole transmission layer 3, a second hole transmission layer 4, a light-emitting layer 5, a first electron transmission layer 6, a second electron transmission layer 7, a cathode 8 (magnesium-silver electrode, a mass ratio of magnesium to silver is 9:1) and a capping layer CPL 9. The ITO anode 2 has a thickness of 15 nm. The first hole transmission layer 3 has a thickness of 10 nm. The second hole transmission layer 4 has a thickness of 95 nm. The light-emitting layer 5 has a thickness of 30 nm. The first electron transmission layer 6 has a thickness of 35 nm. The second electron transmission layer 7 has a thickness of 5 nm. The magnesium-silver electrode 8 has a thickness of 15 nm. The capping layer CPL 9 has a thickness of 100 nm.

In an embodiment, the steps for preparing the organic light-emitting device according to the present disclosure are as follows.

1) A glass substrate 1 was cut into a size of 50 mm×50 mm×0.7 mm, subjected to ultrasonic treatments in isopropyl alcohol and in deionized water for 30 minutes, respectively, and then exposed to ozone for about 10 minutes for cleaning. The obtained glass substrate with an ITO anode 2 was mounted on a vacuum deposition apparatus.

2) A hole injection layer material HAT-CN was evaporated on the ITO anode 2 by vacuum evaporation to obtain a layer having a thickness of 10 nm and used as the first hole transmission layer 3.

3) The material TAPC of the second hole transmission layer 4 was evaporated by vacuum evaporation on the first hole transmission layer 3 to obtain a layer having a thickness of 10 nm and used as the second hole transmission layer 4.

4) The light-emitting layer 5 was co-deposited on the hole transmission layer 4, in which Compound H002 is used as a host material, Ir(ppy)$_3$ is used as a doping material, and a mass ratio of Compound H002 to Ir(ppy)$_3$ is 19:1. The light-emitting layer 5 has a thickness of 30 nm.

5) The material BPen of the first electron transmission layer 6 was evaporated on the light-emitting layer 5 to obtain the first electron transmission layer 6 having a thickness of 35 nm.

6) The material Alq3 of the second electron transmission layer 7 was evaporated by vacuum evaporation on the first electron transmission layer 6 to obtain the second electron transmission layer 7 having a thickness of 5 nm.

7) The magnesium-silver electrode was evaporated by vacuum evaporation on the second electron transmission layer 7 to manufacture the cathode 8 having a thickness of 15 nm, in which the mass ratio of Mg to Ag is 9:1.

8) The hole material CBP having a high refractive index was evaporated by vacuum evaporation on the cathode 8 to form the capping layer (CPL) 9 having a thickness of 100 nm and used as a cathode covering layer.

The compounds and structures involved in this example are listed as follows.

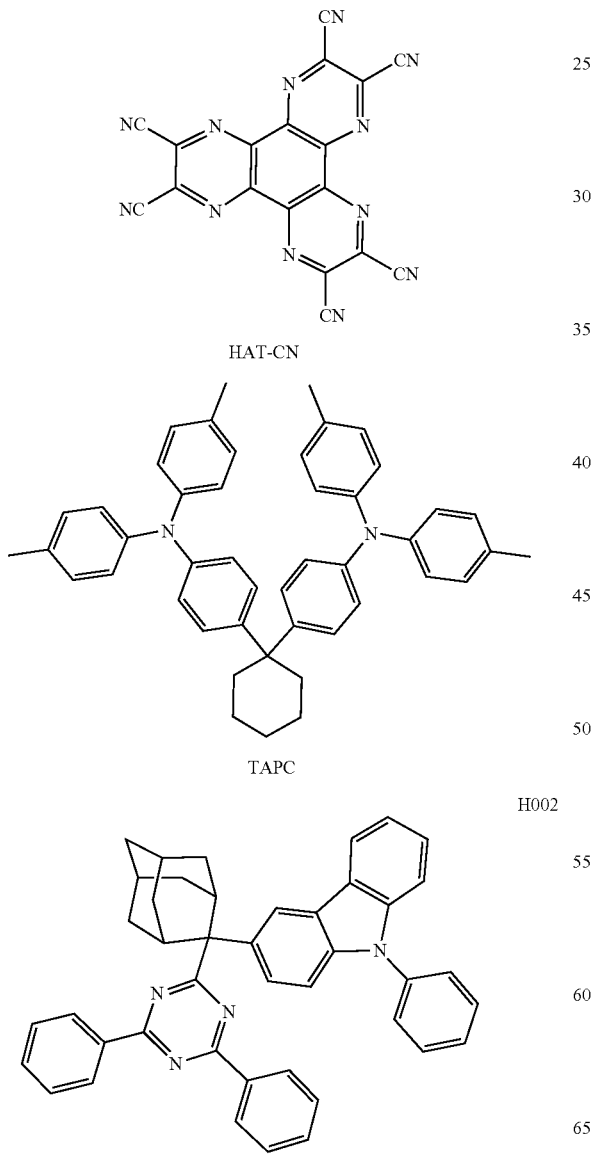

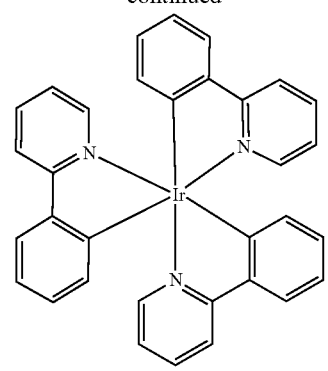

Ir(pyy)3

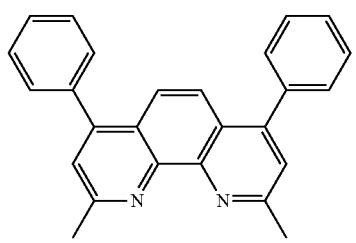

BPen

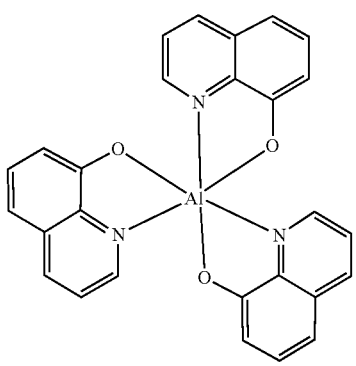

Alq3

CBP

Device Example 2

Device Example 2 differs from Device Example 1 in that the host material is H018. The other materials of other layers are all the same.

Device Example 3

Device Example 3 differs from Device Example 1 in that the host material is H075. The other materials of other layers are all the same.

Device Example 4

Device Example 4 differs from Device Example 1 in that the host material is H077. The other materials of other layers are all the same.

Device Comparative Example 1

Device Comparative Example 1 differs from Device Example 1 in that the host material is CzTRZ. The other materials of other layers are all the same.

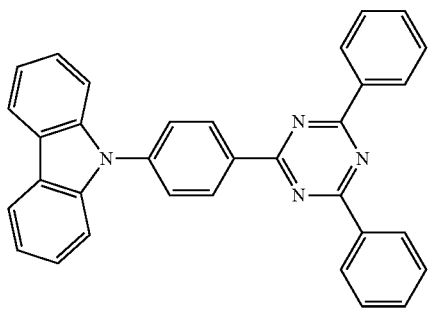

CzTRZ

TABLE 2 characterization of device performance

| No. | Host material | Driving voltage (V) | EQE/% | CE(cd/A) |
|---|---|---|---|---|
| Example1 | H002 | 3.50 | 27.2 | 128.9 |
| Example2 | H018 | 3.12 | 30.3 | 134.7 |
| Example3 | H075 | 3.49 | 31.7 | 120.1 |
| Example4 | H077 | 3.76 | 33.6 | 126.8 |
| Comparative Example 1 | CzTRZ | 4.10 | 24.2 | 103.2 |

As shown in Table 2, the optical devices adopting the compounds of the present disclosure have lower drive voltage, higher current efficiency, and higher luminance than Comparative Example 1.

The present disclosure also provides a display apparatus including the organic light-emitting display panel as described above.

Figure 4:
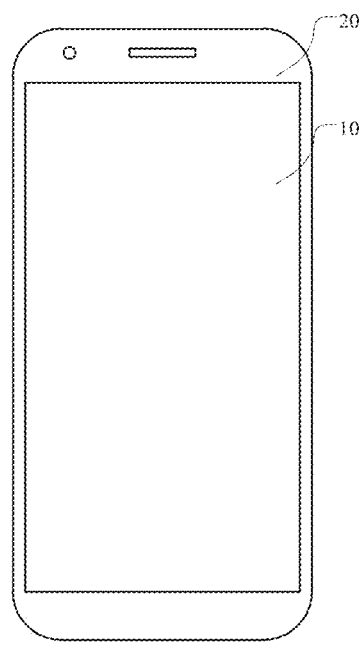
FIG. 4 is a schematic diagram of a display apparatus according to an embodiment of the present disclosure.

In an embodiment, the organic light-emitting device is an OLED, such as an OLED in an organic light-emitting display apparatus. In an embodiment, the organic light-emitting apparatus is a mobile phone display screen, a computer display screen, a liquid crystal television display screen, a smart watch display screen, or a smart car display panel, VR or AR helmet display screen, or display screens of various smart devices. FIG. 4 is a schematic diagram of a display apparatus according to an embodiment of the present disclosure. In FIG. 4, a mobile phone display panel is denoted with reference number 10, a display apparatus is denoted with reference number 20.

The above embodiments of the present disclosure are several preferred embodiments, but not intended to limit the scope of the claims. Any change and modification can be made by those skilled in the art without departing from the scope of the present application, and the protection scope is defined by the claims.

What is claimed is:

1. A compound having a chemical structure according to Formula (I):

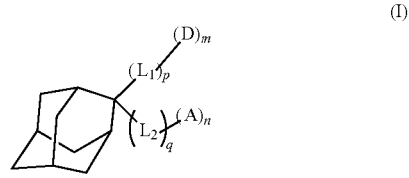

(I)

wherein D is an electron donor, A is an electron acceptor; m is a number of the electron donors D, n is a number of the electron acceptors A, and m and n are each an integer independently selected from 1, 2 and 3; p is a number of $L_1$, q is a number of $L_2$, and p and q are each an integer independently selected from 0, 1, or 2;

$L_1$ and $L_2$ are each independently selected from the group consisting of a single bond, a substituted or unsubstituted C1-C20 alkylene, a substituted or unsubstituted C3-C20 cycloalkylene, a substituted or unsubstituted C3-C20 heterocyclic alkylene, a substituted or unsubstituted C6-C40 arylene, a substituted or unsubstituted C4-C40 heteroarylene, a substituted or unsubstituted C10-C60 fused arylene, a substituted or unsubstituted C10-C60 fused heteroarylene, and combinations thereof;

D is selected from the group consisting of a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C4-C40 heteroaryl, a substituted or unsubstituted C10-C60 fused arylene, a substituted or unsubstituted C10-C60 fused heteroarylene, a substituted or unsubstituted C12-C40 carbazolyl and its derivative groups, a substituted or unsubstituted C12-C40 diphenylamino and its derivative groups, a substituted or unsubstituted C18-C60 triphenylamino and its derivative groups, a substituted or unsubstituted C12-C40 acridinyl and its derivative groups, and combinations thereof; and A is selected from the group consisting of a nitrogen-containing heterocyclic group, a cyano-containing group, a triarylboron-based group, a benzophenone-based group, an aromatic heterocyclic ketone-based group, a sulfone-based group, a phosphoroso-containing groups, and combinations thereof;

wherein L1 and L2 are identical and are phenyl, m and n are each 1;

wherein D is any one of the following groups:

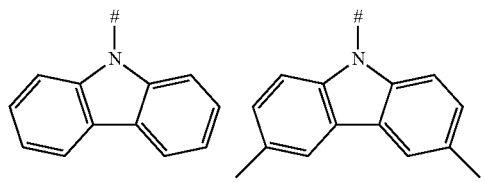

-continued
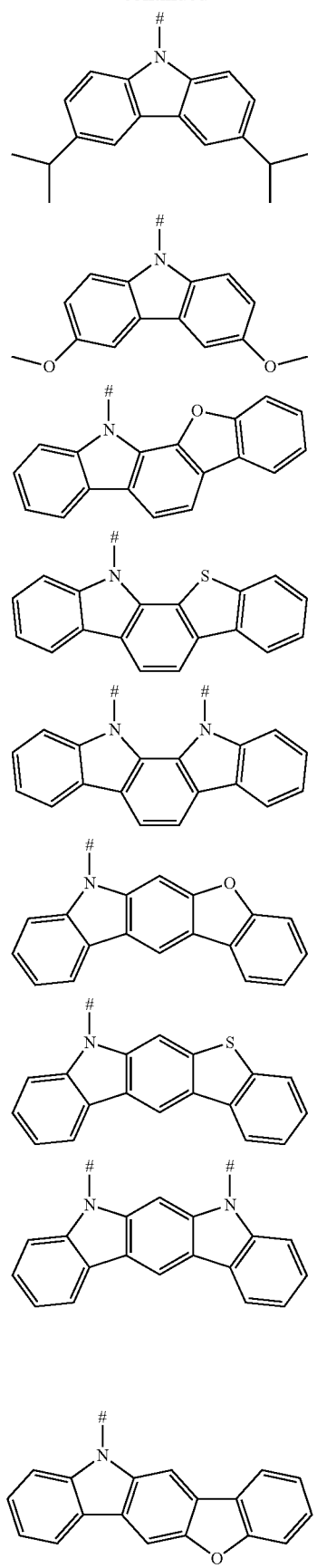
-continued
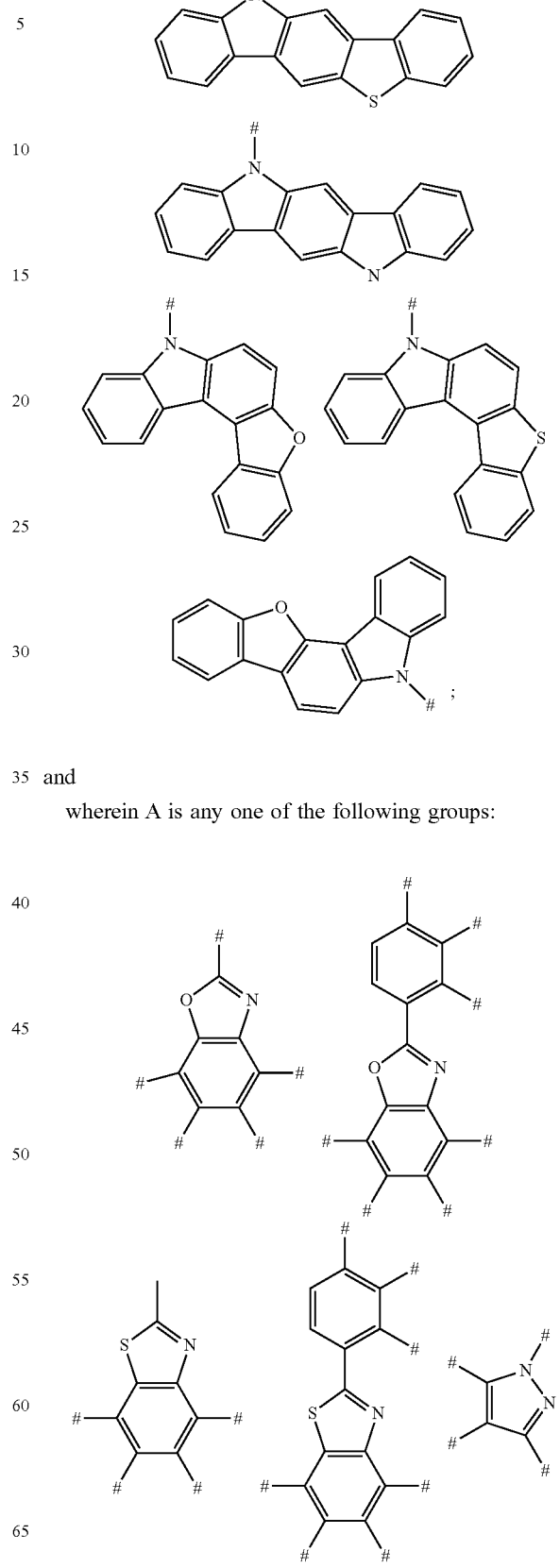
and
wherein A is any one of the following groups:

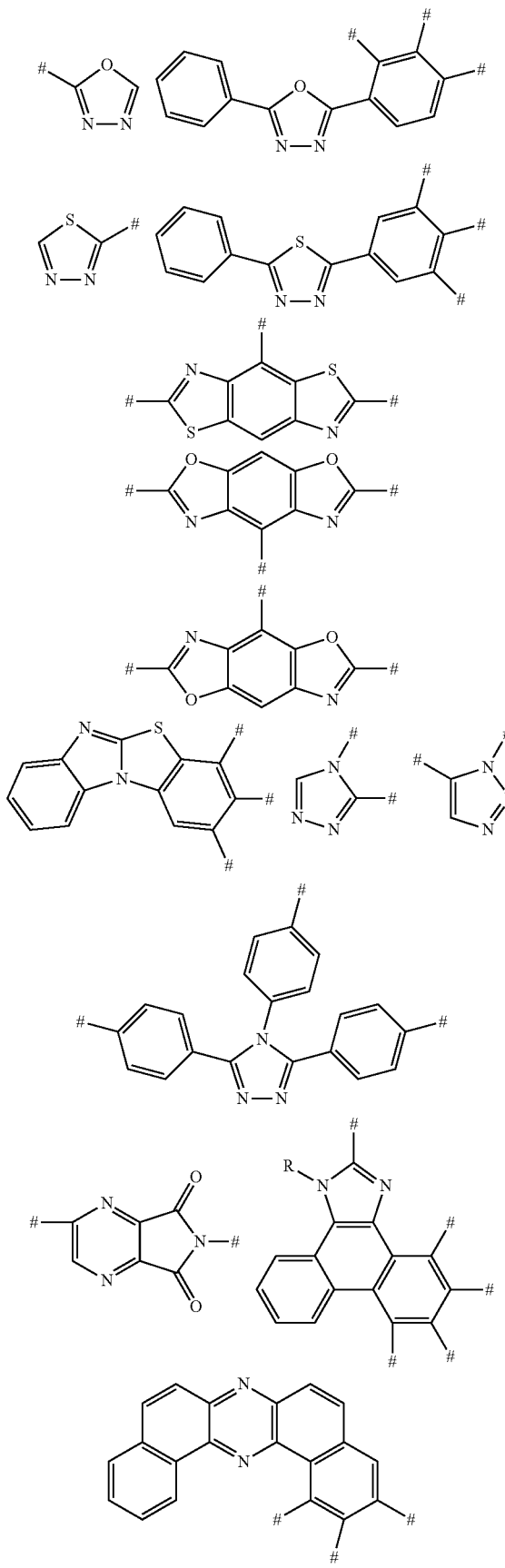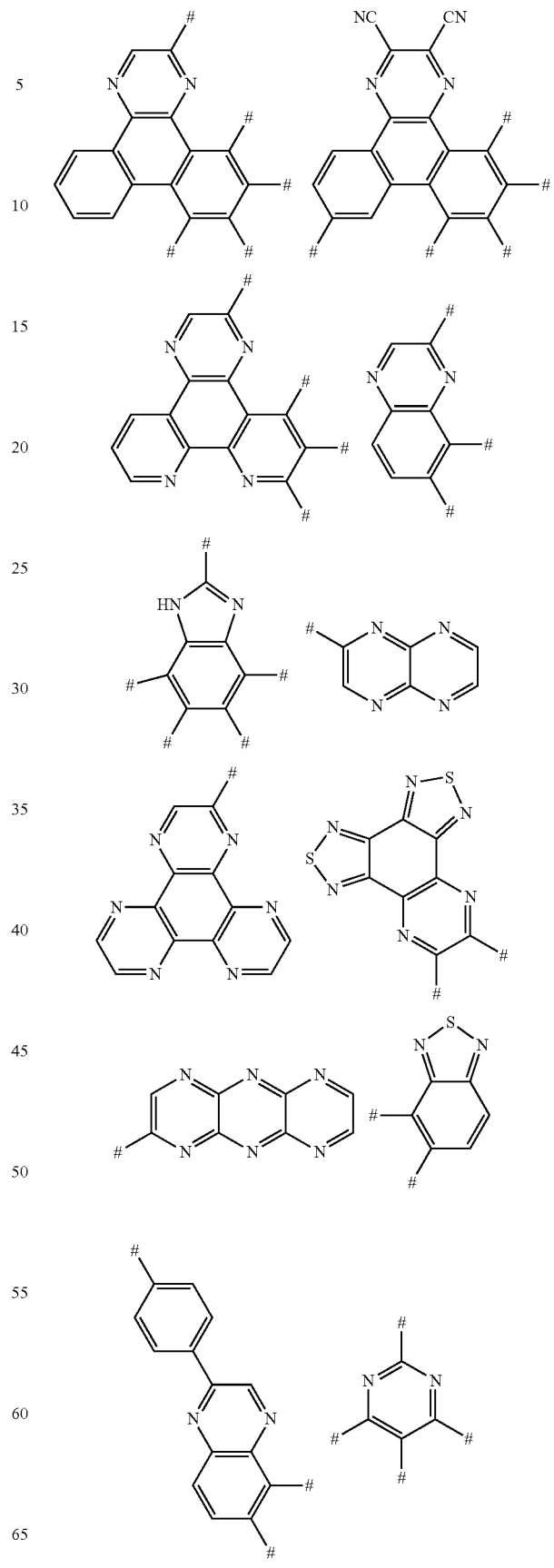

-continued

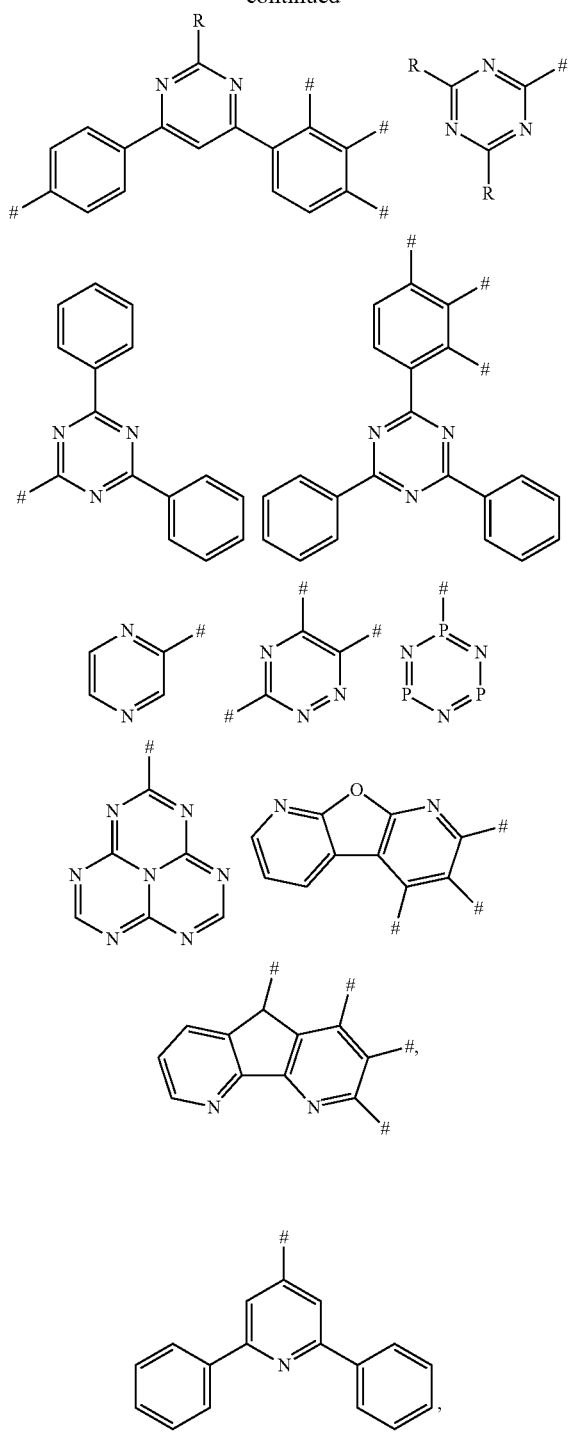

wherein R is selected from the group consisting of a hydrogen atom, C1-C20 alkyl, C1-C20 alkoxy, C4-C8 cycloalkyl, C6-C40 aryl, and C4-C40 heteroaryl; and # indicates a bonding position.

2. The compound according to claim 1, wherein $L_1$ and $L_2$ are different.

3. The compound according to claim 1, wherein p is 0, and q is 1.

4. The compound according to claim 1, wherein D is any one of the following formulas:

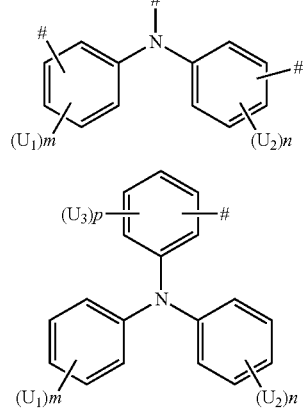

wherein m, n and p are each an integer independently selected from 0, 1, 2 or 3;

$U_1$, $U_2$, and $U_3$ are each independently selected from the group consisting of a hydrogen atom, a substituted or unsubstituted C1-C30 alkyl, a substituted or unsubstituted silylene, a substituted or unsubstituted C3-C20 cycloalkyl, a substituted or unsubstituted C1-C30 alkoxy, a substituted or unsubstituted C6-C30 aryl, a substituted or unsubstituted C10-C30 fused aryl, and combinations thereof; and # indicates a bonding position.

5. The compound according to claim 4, wherein the electron donor D is any one of the following groups:

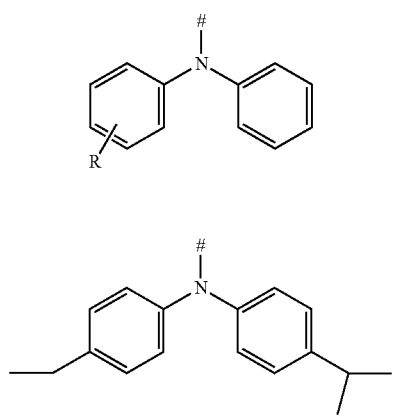

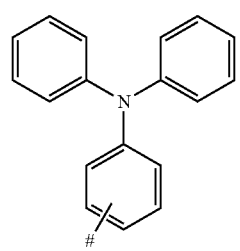

-continued

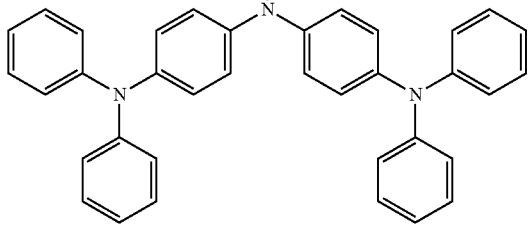

wherein R is selected from the group consisting of a hydrogen atom, a substituted or unsubstituted C1-C20 alkyl, a substituted or unsubstituted silylene, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C10-C30 fused aryl, and a substituted or unsubstituted C4-C40 heteroaryl.

6. The compound according to claim 1, D is any one of the following groups:

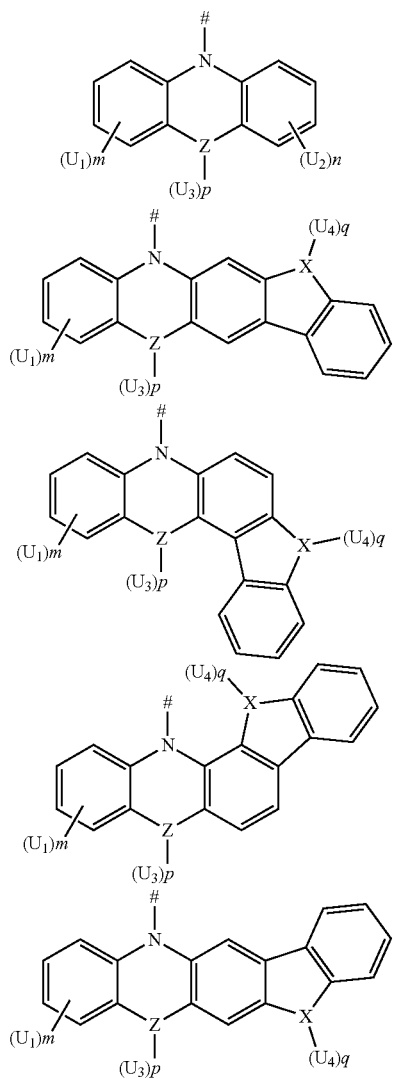

-continued

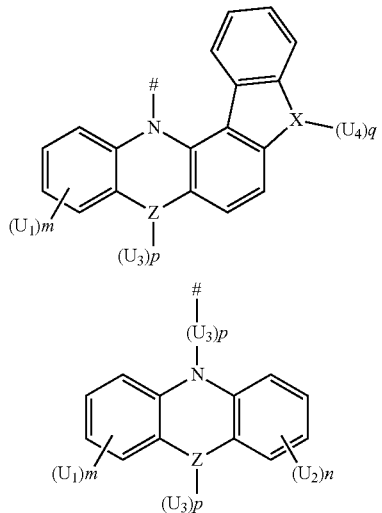

wherein Z is selected from the group consisting of a carbon atom, a nitrogen atom, an oxygen atom, a sulfur atom and a silicon atom;

X is selected from the group consisting of a carbon atom, a nitrogen atom, an oxygen atom and a sulfur atom;

m, n, p and q are each an integer independently selected from 0, 1, 2 or 3;

$U_1$, $U_2$, $U_3$ and $U_4$ are each independently selected from the group consisting of a hydrogen atom, a substituted or unsubstituted C1-C30 alkyl, a substituted or unsubstituted silylene, a substituted or unsubstituted C3-C20 cycloalkyl, a substituted or unsubstituted C1-C30 alkoxy, a substituted or unsubstituted C6-C30 aryl, and a substituted or unsubstituted C10-C30 fused aryl;

when Z or X is an oxygen atom or a sulfur atom, p or q is 0; and # indicates a bonding position.

7. The compound according to claim 6, wherein D is any one of the following groups:

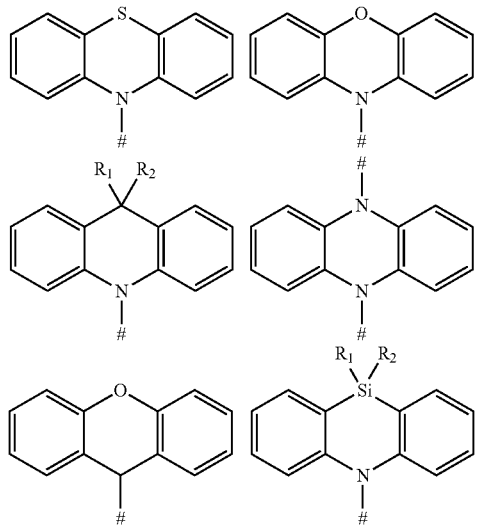

-continued

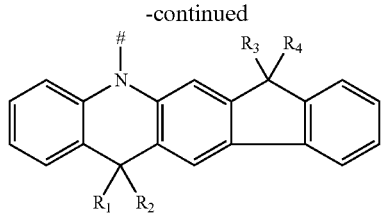

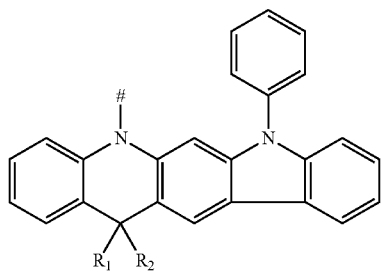

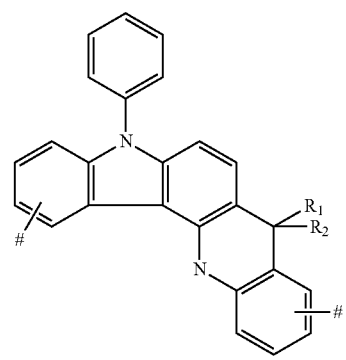

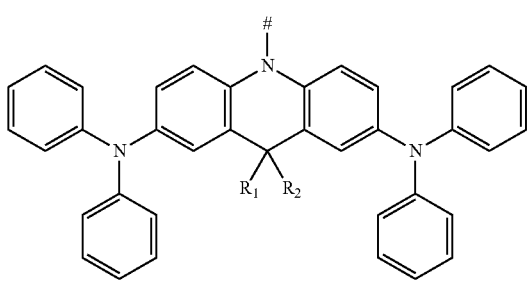

wherein $R_1$, $R_2$, $R_3$ and $R_4$ are each independently selected from the group consisting of a hydrogen atom, a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, and a substituted or unsubstituted C4-C40 heteroaryl.

8. The compound according to claim 1, wherein A is any one of the following groups:

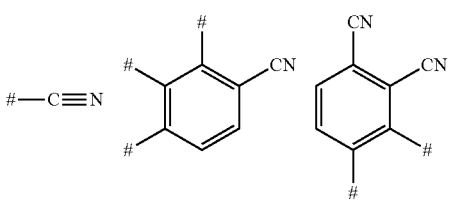

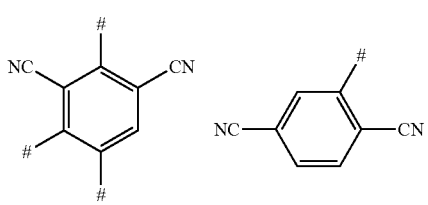

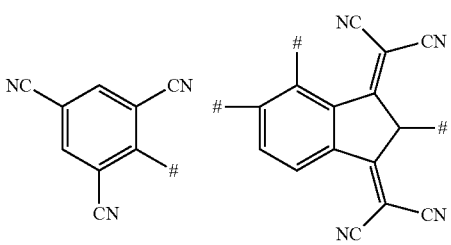

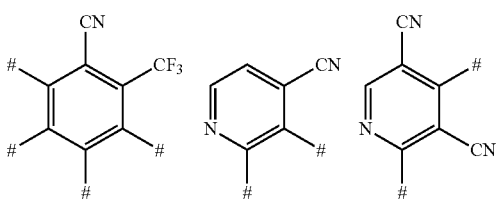

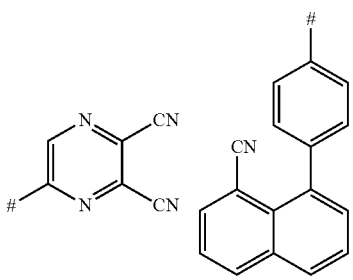

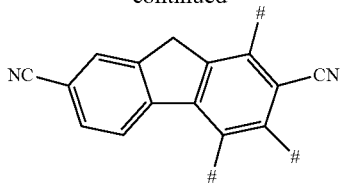
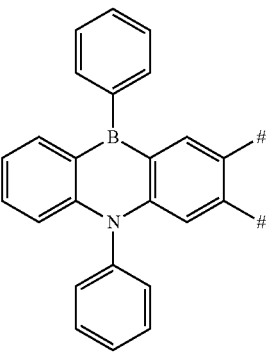
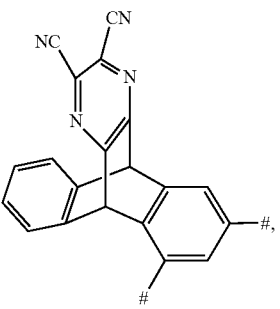
wherein # indicates a bonding position.
9. The compound according to claim 1, wherein A is any one of the following groups:
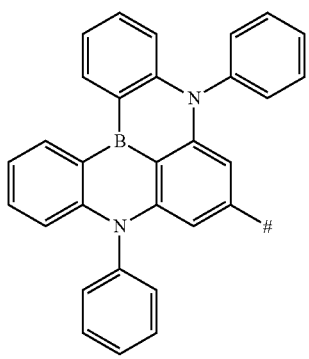
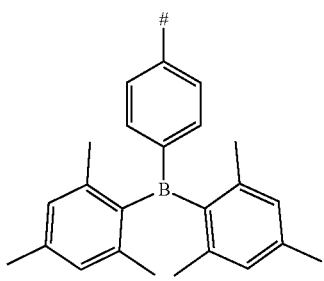
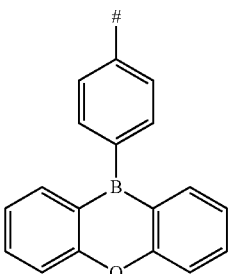 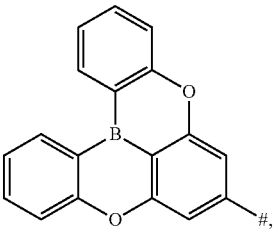
wherein # indicates a bonding position.
10. The compound according to claim 1, wherein A is any one of the following groups:
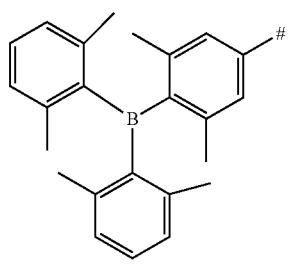
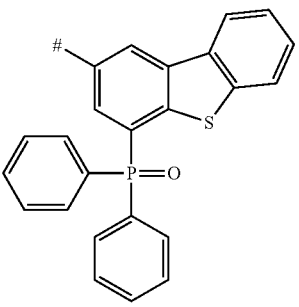
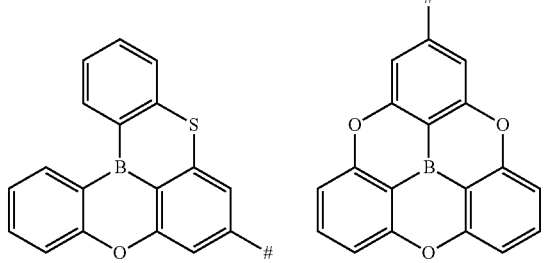

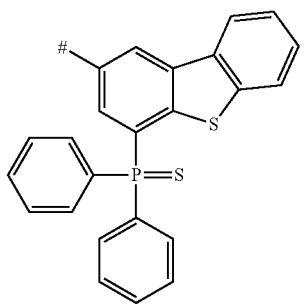

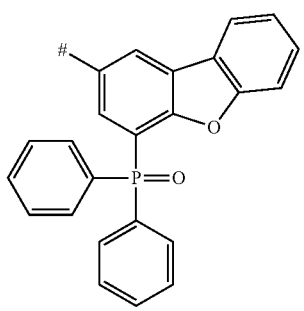

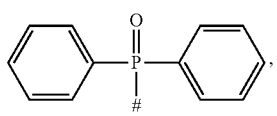

wherein # indicates a bonding position.

11. The compound according to claim 1, wherein the compound is any one of the following compounds:

H073

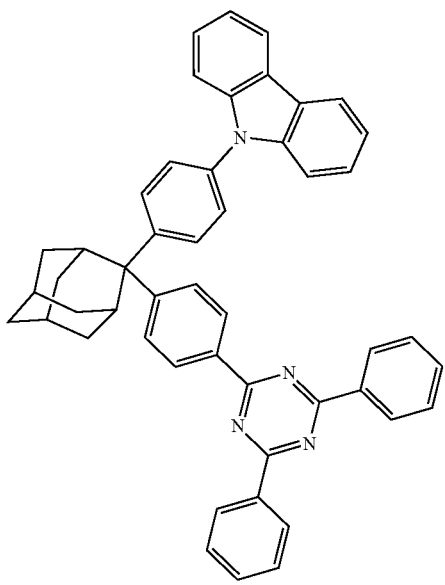

H074

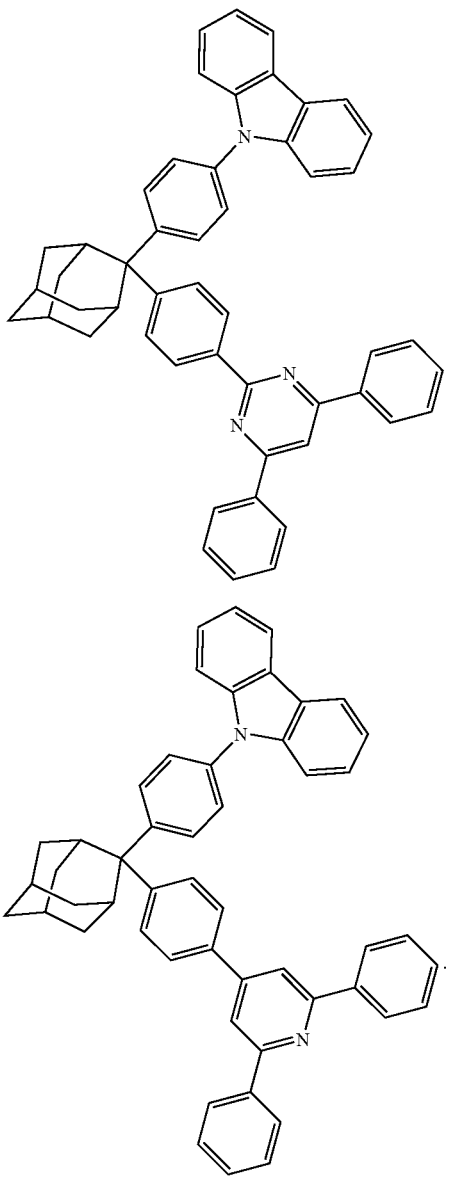

H075

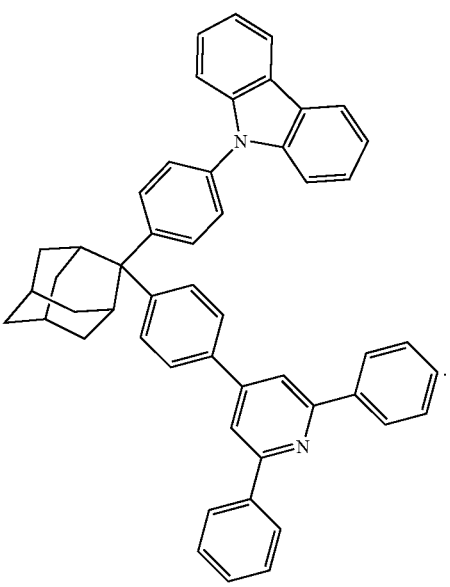

12. A display panel, comprising an organic light-emitting device,
wherein the organic light-emitting device comprises an anode, a cathode arranged opposite to the anode, a capping layer disposed at a side of the cathode facing away from the anode, and an organic layer disposed between the anode and the cathode, the organic layer comprising an electron transmission layer, a hole transmission layer, and a light-emitting layer, wherein at least one of the capping layer, the electron transmission layer, the hole transmission layer, and the light-emitting layer is made of the compound according to claim 1.

13. A display apparatus, comprising the display panel according to claim 12.

* * * * *